US008485185B2

(12) United States Patent
Masic et al.

(10) Patent No.: US 8,485,185 B2
(45) Date of Patent: Jul. 16, 2013

(54) SYSTEMS AND METHODS FOR VENTILATION IN PROPORTION TO PATIENT EFFORT

(75) Inventors: Milenko Masic, San Diego, CA (US); Jon Guy, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 732 days.

(21) Appl. No.: 12/479,259

(22) Filed: Jun. 5, 2009

(65) Prior Publication Data

US 2009/0301491 A1 Dec. 10, 2009

Related U.S. Application Data

(60) Provisional application No. 61/059,599, filed on Jun. 6, 2008, provisional application No. 61/101,575, filed on Sep. 30, 2008, provisional application No. 61/101,578, filed on Sep. 30, 2008.

(51) Int. Cl.
*F16K 31/02* (2006.01)

(52) U.S. Cl.
USPC .............................. 128/204.23; 128/204.21

(58) Field of Classification Search
USPC ... 128/203.12, 203.14, 204.18, 204.21–204.23, 128/204.26; 600/529, 533, 538
See application file for complete search history.

(56) References Cited

U.S. PATENT DOCUMENTS

| | | |
|---|---|---|
| 3,575,167 A | 4/1971 | Michielsen |
| 3,677,267 A | 7/1972 | Richards |
| 3,908,704 A | 9/1975 | Clement et al. |
| 4,095,592 A | 6/1978 | Delphia |
| 4,401,116 A | 8/1983 | Fry et al. |
| 4,421,113 A | 12/1983 | Gedeon et al. |
| 4,444,201 A | 4/1984 | Itoh |
| 4,448,192 A | 5/1984 | Stawitcke et al. |
| 4,702,240 A | 10/1987 | Chaoui |
| 4,721,060 A | 1/1988 | Cannon et al. |
| 4,752,089 A | 6/1988 | Carter |
| 4,790,832 A | 12/1988 | Lopez |
| 4,870,961 A | 10/1989 | Barnard |
| 4,921,642 A | 5/1990 | LaTorraca |

(Continued)

FOREIGN PATENT DOCUMENTS

| | | |
|---|---|---|
| EP | 521515 A1 | 1/1993 |
| EP | 1005829 A1 | 6/2000 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196. (196 pages).

(Continued)

*Primary Examiner* — Kristen Matter

(57) ABSTRACT

Various embodiments of the present disclosure provide systems, methods and devices for respiratory support. As one example, a ventilation system is disclosed that includes a computer readable medium including instructions executable by a processor to receive a measured pressure value and a net flow value. A patient effort value is calculated based on a relationship between patient effort, the measured pressure value and the net flow value. The instructions are further executable to calculate a gas delivery metric that varies as a function of the patient effort value. Gas is then caused to be delivered consistent with the gas delivery metric.

36 Claims, 12 Drawing Sheets

U.S. PATENT DOCUMENTS

| | | |
|---|---|---|
| 4,954,799 A | 9/1990 | Kumar |
| 5,016,626 A | 5/1991 | Jones |
| 5,057,822 A | 10/1991 | Hoffman |
| 5,069,220 A | 12/1991 | Casparie et al. |
| 5,072,737 A | 12/1991 | Goulding |
| 5,074,297 A | 12/1991 | Venegas |
| 5,080,093 A | 1/1992 | Raabe et al. |
| 5,086,767 A | 2/1992 | Legal |
| 5,107,930 A | 4/1992 | Younes |
| 5,117,818 A | 6/1992 | Palfy |
| 5,127,398 A | 7/1992 | Stone |
| 5,129,390 A | 7/1992 | Chopin et al. |
| 5,134,994 A | 8/1992 | Say |
| 5,148,802 A | 9/1992 | Sanders et al. |
| 5,150,291 A | 9/1992 | Cummings et al. |
| 5,161,525 A | 11/1992 | Kimm et al. |
| 5,165,398 A | 11/1992 | Bird |
| 5,174,284 A | 12/1992 | Jackson |
| 5,195,512 A | 3/1993 | Rosso |
| 5,211,170 A | 5/1993 | Press |
| 5,235,973 A | 8/1993 | Levinson |
| 5,237,987 A | 8/1993 | Anderson et al. |
| 5,239,995 A | 8/1993 | Estes et al. |
| 5,259,374 A | 11/1993 | Miller et al. |
| 5,271,389 A | 12/1993 | Isaza et al. |
| 5,273,032 A | 12/1993 | Borody |
| 5,279,549 A | 1/1994 | Ranford |
| 5,299,568 A | 4/1994 | Forare et al. |
| 5,301,921 A | 4/1994 | Kumar |
| 5,303,698 A | 4/1994 | Tobia et al. |
| 5,303,700 A | 4/1994 | Weismann et al. |
| 5,307,794 A | 5/1994 | Rauterkus et al. |
| 5,316,009 A | 5/1994 | Yamada |
| 5,318,017 A | 6/1994 | Ellison |
| 5,319,540 A | 6/1994 | Isaza et al. |
| 5,320,093 A | 6/1994 | Raemer |
| 5,322,057 A | 6/1994 | Raabe et al. |
| 5,323,772 A | 6/1994 | Linden et al. |
| 5,325,861 A | 7/1994 | Goulding |
| 5,333,606 A | 8/1994 | Schneider et al. |
| 5,335,650 A | 8/1994 | Shaffer et al. |
| 5,339,807 A | 8/1994 | Carter |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,368,019 A | 11/1994 | LaTorraca |
| 5,373,842 A | 12/1994 | Olsson et al. |
| 5,383,448 A | 1/1995 | Tkatchouk et al. |
| 5,383,449 A | 1/1995 | Forare et al. |
| 5,385,142 A | 1/1995 | Brady et al. |
| 5,390,666 A | 2/1995 | Kimm et al. |
| 5,395,301 A | 3/1995 | Russek |
| 5,398,676 A | 3/1995 | Press et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,419,314 A | 5/1995 | Christopher |
| 5,429,123 A | 7/1995 | Shaffer et al. |
| 5,429,124 A | 7/1995 | Yoshida et al. |
| 5,433,193 A | 7/1995 | Sanders et al. |
| 5,435,305 A | 7/1995 | Rankin, Sr. |
| 5,438,980 A | 8/1995 | Phillips |
| 5,443,075 A | 8/1995 | Holscher |
| 5,471,977 A | 12/1995 | Olsson et al. |
| 5,474,062 A | 12/1995 | DeVires et al. |
| 5,494,028 A | 2/1996 | DeVries et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,537,999 A | 7/1996 | Dearman et al. |
| 5,540,220 A | 7/1996 | Gropper et al. |
| 5,542,415 A | 8/1996 | Brody |
| 5,542,416 A | 8/1996 | Chalvignac |
| 5,544,674 A | 8/1996 | Kelly |
| 5,549,106 A | 8/1996 | Gruenke et al. |
| 5,551,418 A | 9/1996 | Estes et al. |
| 5,558,086 A | 9/1996 | Smith et al. |
| 5,562,918 A | 10/1996 | Stimpson |
| 5,564,416 A | 10/1996 | Jones |
| 5,582,163 A | 12/1996 | Bonassa |
| 5,590,651 A | 1/1997 | Shaffer et al. |
| 5,596,983 A | 1/1997 | Zander et al. |
| 5,596,984 A | 1/1997 | O'Mahoney et al. |
| 5,603,316 A | 2/1997 | Coufal et al. |
| 5,606,968 A | 3/1997 | Mang |
| 5,630,411 A | 5/1997 | Holscher |
| 5,632,269 A | 5/1997 | Zdrojkowski |
| 5,632,270 A | 5/1997 | O'Mahoney et al. |
| 5,642,726 A | 7/1997 | Owens et al. |
| 5,645,048 A | 7/1997 | Brodsky et al. |
| 5,647,351 A | 7/1997 | Weismann et al. |
| 5,651,361 A | 7/1997 | Dearman et al. |
| 5,655,519 A | 8/1997 | Alfery |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,687,713 A | 11/1997 | Bahr et al. |
| 5,692,497 A | 12/1997 | Schnitzer et al. |
| 5,715,812 A | 2/1998 | Deighan et al. |
| 5,724,962 A | 3/1998 | Vidgren et al. |
| 5,735,267 A | 4/1998 | Tobia |
| 5,740,797 A | 4/1998 | Dickson |
| 5,743,253 A | 4/1998 | Castor et al. ............ 128/200.24 |
| 5,762,480 A | 6/1998 | Adahan |
| 5,765,558 A | 6/1998 | Psaros et al. |
| 5,771,884 A | 6/1998 | Yarnall et al. |
| 5,791,339 A | 8/1998 | Winter |
| 5,794,986 A | 8/1998 | Gansel et al. |
| 5,803,065 A | 9/1998 | Zdrojkowski et al. |
| 5,806,512 A | 9/1998 | Abramov et al. |
| 5,807,245 A | 9/1998 | Aldestam et al. |
| 5,810,000 A | 9/1998 | Stevens |
| 5,813,399 A | 9/1998 | Isaza et al. |
| 5,813,401 A | 9/1998 | Radcliff et al. |
| 5,814,086 A | 9/1998 | Hirschberg et al. |
| 5,826,575 A | 10/1998 | Lall |
| 5,829,441 A | 11/1998 | Kidd et al. |
| 5,836,300 A | 11/1998 | Mault |
| 5,864,938 A | 2/1999 | Gansel et al. |
| 5,865,168 A | 2/1999 | Isaza |
| 5,868,133 A | 2/1999 | DeVries et al. |
| 5,876,352 A | 3/1999 | Weismann |
| 5,878,744 A | 3/1999 | Pfeiffer ................... 128/204.23 |
| 5,881,717 A | 3/1999 | Isaza |
| 5,881,723 A | 3/1999 | Wallace |
| 5,881,725 A | 3/1999 | Hoffman et al. |
| 5,884,623 A | 3/1999 | Winter |
| 5,906,203 A | 5/1999 | Klockseth et al. |
| 5,909,731 A | 6/1999 | O'Mahony et al. |
| 5,911,218 A | 6/1999 | DiMarco |
| 5,915,379 A | 6/1999 | Wallace |
| 5,915,380 A | 6/1999 | Wallace |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,931,160 A | 8/1999 | Gilmore et al. |
| 5,931,162 A | 8/1999 | Christian |
| 5,934,274 A | 8/1999 | Merrick et al. |
| 5,937,853 A | 8/1999 | Strom |
| 5,944,680 A | 8/1999 | Christopherson et al. |
| 5,970,975 A | 10/1999 | Estes et al. |
| 5,996,580 A | 12/1999 | Swann |
| 6,000,396 A | 12/1999 | Melker et al. |
| 6,015,388 A | 1/2000 | Sackner et al. |
| 6,019,100 A | 2/2000 | Alving et al. |
| 6,024,089 A | 2/2000 | Wallace |
| 6,029,664 A | 2/2000 | Zdrojkowski et al. |

| | | | |
|---|---|---|---|
| 6,041,780 A | 3/2000 | Richard et al. | |
| 6,047,860 A | 4/2000 | Sanders | |
| 6,068,602 A | 5/2000 | Tham et al. | |
| 6,076,523 A | 6/2000 | Jones et al. | |
| 6,095,140 A | 8/2000 | Poon et al. | |
| 6,109,260 A | 8/2000 | Bathe | |
| 6,112,744 A | 9/2000 | Hognelid | |
| 6,116,240 A | 9/2000 | Merrick et al. | |
| 6,116,464 A | 9/2000 | Sanders | |
| 6,123,073 A | 9/2000 | Schlawin et al. | |
| 6,131,571 A | 10/2000 | Lampotang et al. | |
| 6,131,572 A | 10/2000 | Heinonen | |
| 6,135,105 A | 10/2000 | Lampotang et al. | |
| 6,135,106 A | 10/2000 | Dirks et al. | |
| 6,135,107 A | 10/2000 | Mault | |
| 6,135,967 A | 10/2000 | Fiorenza et al. | |
| 6,142,150 A | 11/2000 | O'Mahoney et al. | |
| 6,148,814 A | 11/2000 | Clemmer et al. | |
| 6,152,129 A | 11/2000 | Berthon Jones | |
| 6,152,133 A | 11/2000 | Psaros et al. | |
| 6,152,135 A | 11/2000 | DeVries et al. | |
| 6,155,257 A | 12/2000 | Lurie et al. | |
| 6,158,432 A | 12/2000 | Biondi et al. | |
| 6,158,433 A | 12/2000 | Ong et al. | |
| 6,161,539 A | 12/2000 | Winter | |
| 6,192,885 B1 | 2/2001 | Jalde | |
| 6,196,222 B1 | 3/2001 | Heinonen et al. | |
| 6,213,119 B1 | 4/2001 | Brydon et al. | |
| 6,220,245 B1 | 4/2001 | Takabayashi et al. | |
| 6,230,708 B1 | 5/2001 | Radko | |
| 6,257,234 B1 | 7/2001 | Sun | |
| 6,260,549 B1 | 7/2001 | Sosiak | |
| 6,269,812 B1 | 8/2001 | Wallace | |
| 6,273,444 B1 | 8/2001 | Power | |
| 6,279,569 B1 | 8/2001 | Berthon Jones | |
| 6,279,574 B1 | 8/2001 | Richardson et al. | |
| 6,283,119 B1 | 9/2001 | Bourdon | |
| 6,305,373 B1 | 10/2001 | Wallace | |
| 6,305,374 B1 | 10/2001 | Zdrojkowski et al. | |
| 6,308,703 B1 | 10/2001 | Alving et al. | |
| 6,308,706 B1 | 10/2001 | Lammers et al. | |
| 6,309,360 B1 | 10/2001 | Mault | |
| 6,321,748 B1 | 11/2001 | O'Mahoney | |
| 6,325,785 B1 | 12/2001 | Babkes et al. | |
| 6,343,603 B1 | 2/2002 | Tuck et al. | |
| 6,345,619 B1 | 2/2002 | Finn | |
| 6,357,438 B1 | 3/2002 | Hansen | |
| 6,360,740 B1 | 3/2002 | Ward et al. | |
| 6,360,745 B1 | 3/2002 | Wallace | |
| 6,369,838 B1 | 4/2002 | Wallace et al. | |
| 6,390,091 B1 | 5/2002 | Banner et al. | |
| 6,390,988 B1 | 5/2002 | Robinson | |
| 6,408,847 B1 | 6/2002 | Nuckols et al. | |
| 6,412,482 B1 | 7/2002 | Rowe | |
| 6,412,483 B1 | 7/2002 | Jones et al. | |
| 6,425,392 B1 | 7/2002 | Sosiak | |
| 6,439,229 B1 | 8/2002 | Du et al. | |
| 6,450,968 B1 | 9/2002 | Wallen et al. | |
| 6,461,315 B1 | 10/2002 | Gattinoni | |
| 6,463,930 B2 | 10/2002 | Biondi et al. | |
| 6,467,478 B1 | 10/2002 | Merrick et al. | |
| 6,467,479 B1 | 10/2002 | Albert et al. | |
| 6,484,719 B1 | 11/2002 | Berthon-Jones | |
| 6,494,201 B1 | 12/2002 | Welik | |
| 6,516,800 B1 | 2/2003 | Bowden | |
| 6,523,538 B1 | 2/2003 | Wikefeldt | |
| 6,526,970 B2 | 3/2003 | DeVries et al. | |
| 6,532,956 B2 | 3/2003 | Hill | |
| 6,532,957 B2 | 3/2003 | Berthon-Jones | |
| 6,532,959 B1 | 3/2003 | Berthon Jones | |
| 6,539,938 B2 | 4/2003 | Weinstein et al. | |
| 6,539,940 B2 | 4/2003 | Zdrojkowski et al. | |
| 6,546,930 B1 | 4/2003 | Emerson et al. | |
| 6,547,743 B2 | 4/2003 | Brydon | |
| 6,553,991 B1 | 4/2003 | Isaza | |
| 6,553,992 B1 | 4/2003 | Berthon-Jones et al. | |
| 6,557,553 B1 | 5/2003 | Borrelio | |
| 6,564,798 B1 | 5/2003 | Jalde | |
| 6,571,795 B2 | 6/2003 | Bourdon | |
| 6,571,796 B2 | 6/2003 | Banner et al. | |
| 6,572,561 B2 | 6/2003 | Mault | |
| 6,575,163 B1 | 6/2003 | Berthon-Jones | |
| 6,575,164 B1 | 6/2003 | Jaffe et al. | |
| 6,578,575 B1 | 6/2003 | Jonson | |
| 6,581,599 B1 | 6/2003 | Stenzler | |
| 6,584,973 B1 | 7/2003 | Biondi et al. | |
| 6,588,423 B1 | 7/2003 | Sinderby | |
| 6,595,213 B2 | 7/2003 | Bennarsten | |
| 6,601,583 B2 | 8/2003 | Pessala et al. | |
| 6,609,517 B1 | 8/2003 | Estes et al. | |
| 6,609,518 B2 | 8/2003 | Lamb | |
| 6,616,615 B2 | 9/2003 | Mault | |
| 6,622,726 B1 | 9/2003 | Du et al. | |
| 6,626,175 B2 | 9/2003 | Jafari et al. | 128/204.21 |
| 6,631,716 B1 | 10/2003 | Robinson et al. | |
| 6,631,717 B1 | 10/2003 | Rich et al. | |
| 6,644,310 B1 | 11/2003 | Delache et al. | |
| 6,651,652 B1 | 11/2003 | Ward | |
| 6,659,101 B2 | 12/2003 | Berthon Jones | |
| 6,659,961 B2 | 12/2003 | Robinson | |
| 6,668,824 B1 | 12/2003 | Isaza et al. | |
| 6,668,829 B2 | 12/2003 | Biondi et al. | |
| 6,675,801 B2 | 1/2004 | Wallace | |
| 6,679,258 B1 | 1/2004 | Ström | |
| 6,681,643 B2 | 1/2004 | Heinonen | |
| 6,688,307 B2 | 2/2004 | Berthon-Jones | |
| 6,689,091 B2 | 2/2004 | Bui et al. | |
| 6,694,978 B1 | 2/2004 | Bennarsten | |
| 6,718,974 B1 | 4/2004 | Moberg | |
| 6,722,360 B2 | 4/2004 | Doshi | |
| 6,725,447 B1 | 4/2004 | Gilman et al. | |
| 6,726,598 B1 | 4/2004 | Jarvis et al. | |
| 6,739,337 B2 | 5/2004 | Isaza | |
| 6,745,771 B2 | 6/2004 | Castor et al. | |
| 6,745,773 B1 | 6/2004 | Gobel | |
| 6,752,766 B2 | 6/2004 | Kowallik et al. | |
| 6,752,772 B2 | 6/2004 | Kahn | |
| 6,755,193 B2 | 6/2004 | Berthon Jones et al. | |
| 6,758,216 B1 | 7/2004 | Berthon Jones et al. | |
| 6,761,167 B1 | 7/2004 | Nadjafizadeh et al. | |
| 6,761,168 B1 | 7/2004 | Nadjafizadeh et al. | |
| 6,763,829 B2 | 7/2004 | Jaffe et al. | |
| 6,786,217 B2 | 9/2004 | Stenzler | |
| 6,796,305 B1 | 9/2004 | Banner et al. | |
| 6,805,118 B2 | 10/2004 | Brooker et al. | |
| 6,810,876 B2 | 11/2004 | Berthon-Jones | |
| 6,814,074 B1 | 11/2004 | Nadjafizadeh et al. | |
| 6,814,075 B2 | 11/2004 | Boussignac | |
| 6,820,613 B2 | 11/2004 | Wenkebach et al. | |
| 6,820,618 B2 | 11/2004 | Banner et al. | |
| 6,823,866 B2 | 11/2004 | Jafari et al. | 128/204.21 |
| 6,834,647 B2 | 12/2004 | Blair et al. | |
| 6,837,241 B2 | 1/2005 | Samzelius | |
| 6,837,242 B2 | 1/2005 | Younes | |
| 6,840,240 B1 | 1/2005 | Berthon-Jones et al. | |
| 6,848,444 B2 | 2/2005 | Smith et al. | |
| 6,851,427 B1 | 2/2005 | Nashed | |
| 6,860,264 B2 | 3/2005 | Christopher | |
| 6,860,265 B1 | 3/2005 | Emerson | |
| 6,860,266 B2 | 3/2005 | Blike | |
| 6,860,858 B2 | 3/2005 | Green et al. | |
| 6,866,040 B1 | 3/2005 | Bourdon | |
| 6,877,511 B2 | 4/2005 | Devries et al. | |
| 6,910,480 B1 | 6/2005 | Berthon-Jones | |
| 6,920,875 B1 | 7/2005 | Hill et al. | |
| 6,948,497 B2 | 9/2005 | Zdrojkowski et al. | |
| 6,960,854 B2 | 11/2005 | Nadjafizadeh et al. | |
| 6,976,487 B1 | 12/2005 | Melker et al. | |
| 6,990,980 B2 | 1/2006 | Richey, II | |
| 6,997,881 B2 | 2/2006 | Green et al. | |
| 7,000,612 B2 | 2/2006 | Jafari et al. | 128/204.21 |
| 7,001,339 B2 | 2/2006 | Lin | |
| 7,001,340 B2 | 2/2006 | Lin | |
| 7,011,091 B2 | 3/2006 | Hill et al. | |
| 7,013,892 B2 | 3/2006 | Estes et al. | |
| 7,017,574 B2 | 3/2006 | Biondi et al. | |
| 7,036,504 B2 | 5/2006 | Wallace | |
| 7,040,321 B2 | 5/2006 | Gobel et al. | |

| Patent | Date | Inventor |
|---|---|---|
| 7,051,736 B2 | 5/2006 | Banner et al. |
| 7,055,522 B2 | 6/2006 | Berthon-Jones |
| 7,066,173 B2 | 6/2006 | Banner et al. |
| 7,066,176 B2 | 6/2006 | Jaffe et al. |
| 7,077,131 B2 | 7/2006 | Hansen |
| 7,080,646 B2 | 7/2006 | Wiesmann et al. |
| RE39,225 E | 8/2006 | Isaza et al. |
| 7,100,607 B2 | 9/2006 | Zdrojkowski et al. |
| 7,100,609 B2 | 9/2006 | Berthon Jones et al. |
| 7,117,438 B2 | 10/2006 | Wallace et al. |
| 7,121,277 B2 | 10/2006 | Ström |
| 7,128,069 B2 | 10/2006 | Farrugia et al. |
| 7,137,389 B2 | 11/2006 | Berthon-Jones |
| 7,156,095 B2 | 1/2007 | Melker et al. |
| 7,162,296 B2 | 1/2007 | Leonhardt et al. |
| 7,191,780 B2 | 3/2007 | Faram |
| 7,210,478 B2 | 5/2007 | Banner et al. |
| 7,226,427 B2 | 6/2007 | Steen |
| 7,255,103 B2 | 8/2007 | Bassin |
| 7,270,126 B2 | 9/2007 | Wallace et al. |
| 7,275,540 B2 | 10/2007 | Bolam et al. |
| 7,322,937 B2 | 1/2008 | Blomberg et al. |
| 7,334,578 B2 | 2/2008 | Biondi et al. |
| 7,334,581 B2 | 2/2008 | Doshi |
| 7,347,205 B2 | 3/2008 | Levi |
| 7,363,925 B2 | 4/2008 | Pagan |
| 7,367,337 B2 | 5/2008 | Berthon Jones et al. |
| 7,369,757 B2 | 5/2008 | Farbarik |
| 7,370,650 B2 | 5/2008 | Nadjafizadeh et al. |
| 7,422,015 B2 | 9/2008 | Delisle et al. |
| 7,425,201 B2 | 9/2008 | Euliano et al. |
| 7,428,902 B2 | 9/2008 | Du et al. |
| 7,445,006 B2 | 11/2008 | Dhuper et al. |
| 7,460,959 B2 | 12/2008 | Jafari |
| 7,464,711 B2 | 12/2008 | Flodin |
| 7,465,275 B2 | 12/2008 | Stenqvist |
| 7,484,508 B2 | 2/2009 | Younes |
| 7,487,773 B2 | 2/2009 | Li |
| 7,487,774 B2 | 2/2009 | Acker |
| 7,487,775 B2 | 2/2009 | Mashak |
| 7,509,957 B2 | 3/2009 | Duquette et al. |
| 7,523,752 B2 | 4/2009 | Montgomery et al. |
| 7,530,353 B2 | 5/2009 | Choncholas et al. |
| 7,549,421 B2 | 6/2009 | Levi et al. |
| 7,556,038 B2 | 7/2009 | Kirby et al. |
| 7,559,326 B2 | 7/2009 | Smith et al. |
| 7,572,225 B2 | 8/2009 | Stahmann et al. |
| 7,574,246 B2 | 8/2009 | Krebs et al. |
| 7,584,752 B2 | 9/2009 | Garber et al. |
| 7,588,033 B2 | 9/2009 | Wondka |
| 7,588,543 B2 | 9/2009 | Euliano et al. |
| 7,594,508 B2 | 9/2009 | Doyle |
| 7,610,914 B2 | 11/2009 | Bolam et al. |
| 7,617,821 B2 | 11/2009 | Hughes |
| 7,617,825 B2 | 11/2009 | Pedemonte |
| 7,624,736 B2 | 12/2009 | Borody |
| 7,634,998 B1 | 12/2009 | Fenley |
| 7,644,713 B2 | 1/2010 | Berthon Jones |
| 7,654,802 B2 | 2/2010 | Crawford, Jr. et al. |
| 7,669,594 B2 | 3/2010 | Downie |
| 7,669,598 B2 | 3/2010 | Rick et al. |
| 7,678,061 B2 | 3/2010 | Lee et al. |
| 7,694,677 B2 | 4/2010 | Tang |
| 7,694,682 B2 | 4/2010 | Petersen et al. |
| 7,717,110 B2 | 5/2010 | Kane et al. |
| 7,717,113 B2 | 5/2010 | Andrieux |
| 7,721,736 B2 | 5/2010 | Urias et al. |
| 7,722,546 B2 | 5/2010 | Madaus et al. |
| D618,356 S | 6/2010 | Ross |
| 7,727,160 B2 | 6/2010 | Green et al. |
| 7,731,663 B2 | 6/2010 | Averina et al. |
| 7,775,207 B2 | 8/2010 | Jaffe et al. |
| 7,784,461 B2 | 8/2010 | Figueiredo et al. |
| 7,798,145 B2 | 9/2010 | Weismann et al. |
| 7,802,571 B2 | 9/2010 | Tehrani |
| 7,809,442 B2 | 10/2010 | Bolea et al. |
| 7,814,906 B2 | 10/2010 | Moretti |
| 7,819,815 B2 | 10/2010 | Younes |
| 7,823,588 B2 | 11/2010 | Hansen |
| 7,841,341 B2 | 11/2010 | Dhuper et al. |
| 7,855,716 B2 | 12/2010 | McCreary et al. |
| 7,865,244 B2 | 1/2011 | Giftakis et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,987,847 B2 | 8/2011 | Wickham et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0004893 A1 | 6/2001 | Biondi et al. |
| 2001/0007255 A1 | 7/2001 | Stumpf |
| 2002/0023640 A1 | 2/2002 | Nightengale |
| 2002/0026941 A1 | 3/2002 | Biondi et al. |
| 2002/0046753 A1 | 4/2002 | Lamb |
| 2002/0073993 A1 | 6/2002 | Weinstein et al. |
| 2002/0174866 A1 | 11/2002 | Orr et al. |
| 2002/0185126 A1 | 12/2002 | Krebs |
| 2002/0195105 A1 | 12/2002 | Blue et al. |
| 2003/0010339 A1 | 1/2003 | Banner et al. |
| 2003/0034031 A1 | 2/2003 | Lev et al. |
| 2003/0037786 A1 | 2/2003 | Biondi et al. |
| 2003/0050568 A1 | 3/2003 | Green et al. |
| 2003/0125662 A1 | 7/2003 | Bui |
| 2003/0131848 A1 | 7/2003 | Stenzler |
| 2003/0136402 A1 | 7/2003 | Jiang et al. |
| 2003/0140924 A1 | 7/2003 | Ayslworth et al. |
| 2003/0145853 A1 | 8/2003 | Muellner |
| 2003/0154979 A1 | 8/2003 | Berthon Jones |
| 2003/0159695 A1 | 8/2003 | Younes |
| 2003/0172929 A1 | 9/2003 | Muellner |
| 2003/0178024 A1 | 9/2003 | Allan et al. |
| 2003/0192542 A1 | 10/2003 | Isaza |
| 2003/0192544 A1 | 10/2003 | Berthon Jones et al. |
| 2003/0230307 A1 | 12/2003 | Devries et al. |
| 2004/0016431 A1 | 1/2004 | Preveyraud |
| 2004/0040560 A1 | 3/2004 | Euliano et al. |
| 2004/0050387 A1 | 3/2004 | Younes |
| 2004/0103896 A1 | 6/2004 | Jafari et al. |
| 2004/0159323 A1 | 8/2004 | Schmidt et al. |
| 2004/0187864 A1 | 9/2004 | Adams |
| 2004/0194779 A1 | 10/2004 | Doshi |
| 2004/0194780 A1 | 10/2004 | Doshi |
| 2004/0200477 A1 | 10/2004 | Bleys et al. |
| 2004/0206355 A1 | 10/2004 | Berthon Jones et al. |
| 2004/0221847 A1 | 11/2004 | Berthon Jones et al. |
| 2004/0231670 A1 | 11/2004 | Bassin |
| 2004/0249301 A1 | 12/2004 | Stenqvist |
| 2005/0022809 A1 | 2/2005 | Wondka |
| 2005/0027252 A1 | 2/2005 | Boukas |
| 2005/0039748 A1 | 2/2005 | Andrieux |
| 2005/0061318 A1 | 3/2005 | Faram |
| 2005/0076907 A1 | 4/2005 | Stenzler |
| 2005/0087190 A1* | 4/2005 | Jafari et al. ............. 128/204.21 |
| 2005/0098179 A1 | 5/2005 | Burton et al. |
| 2005/0103331 A1 | 5/2005 | Wedemeyer |
| 2005/0109339 A1 | 5/2005 | Stahmann et al. |
| 2005/0109340 A1 | 5/2005 | Tehrani |

| | | |
|---|---|---|
| 2005/0126565 A1 | 6/2005 | Huang |
| 2005/0133028 A1 | 6/2005 | Pagan |
| 2005/0139212 A1 | 6/2005 | Bourdon |
| 2005/0199237 A1 | 9/2005 | Lurie |
| 2005/0217671 A1 | 10/2005 | Fisher et al. |
| 2005/0241639 A1 | 11/2005 | Zilberg |
| 2005/0263152 A1 | 12/2005 | Fong |
| 2005/0279358 A1 | 12/2005 | Richey, II |
| 2005/0284469 A1 | 12/2005 | Tobia et al. |
| 2006/0011195 A1 | 1/2006 | Zarychta |
| 2006/0032497 A1 | 2/2006 | Doshi |
| 2006/0037614 A1 | 2/2006 | Madaus et al. |
| 2006/0079799 A1 | 4/2006 | Green et al. |
| 2006/0094972 A1 | 5/2006 | Drew |
| 2006/0102180 A1 | 5/2006 | Berthon-Jones |
| 2006/0150974 A1 | 7/2006 | Berthon-Jones |
| 2006/0162727 A1 | 7/2006 | Biondi et al. |
| 2006/0178245 A1 | 8/2006 | Schiller et al. |
| 2006/0201507 A1 | 9/2006 | Breen |
| 2006/0249148 A1 | 11/2006 | Younes |
| 2006/0249155 A1 | 11/2006 | Gambone |
| 2006/0272642 A1 | 12/2006 | Chalvignac |
| 2006/0276718 A1 | 12/2006 | Madaus et al. |
| 2006/0278221 A1 | 12/2006 | Schermeier et al. |
| 2006/0278224 A1 | 12/2006 | Shaffer et al. |
| 2006/0283450 A1 | 12/2006 | Shissler et al. |
| 2006/0283451 A1 | 12/2006 | Albertelli |
| 2007/0000494 A1 | 1/2007 | Banner et al. |
| 2007/0017515 A1 | 1/2007 | Wallace |
| 2007/0017518 A1 | 1/2007 | Farrugia et al. |
| 2007/0028920 A1 | 2/2007 | Acker |
| 2007/0028921 A1 | 2/2007 | Banner et al. |
| 2007/0044796 A1 | 3/2007 | Zdrojkowski et al. |
| 2007/0062529 A1 | 3/2007 | Choncholas et al. |
| 2007/0062530 A1 | 3/2007 | Weismann et al. |
| 2007/0073169 A1 | 3/2007 | Averina et al. |
| 2007/0077200 A1 | 4/2007 | Baker |
| 2007/0089738 A1 | 4/2007 | Soliman et al. |
| 2007/0107728 A1 | 5/2007 | Ricciardelli et al. |
| 2007/0113843 A1 | 5/2007 | Hughes |
| 2007/0144521 A1 | 6/2007 | Devries et al. |
| 2007/0144523 A1 | 6/2007 | Bolam et al. |
| 2007/0151563 A1 | 7/2007 | Ozaki et al. |
| 2007/0163590 A1 | 7/2007 | Bassin |
| 2007/0181122 A1 | 8/2007 | Mulier |
| 2007/0186928 A1 | 8/2007 | Be'Eri |
| 2007/0191787 A1 | 8/2007 | Lim et al. |
| 2007/0193579 A1 | 8/2007 | Duquette et al. |
| 2007/0208267 A1 | 9/2007 | Schmid et al. |
| 2007/0221222 A1 | 9/2007 | Lurie |
| 2007/0225623 A1 | 9/2007 | Freeman |
| 2007/0227537 A1 | 10/2007 | Bemister et al. |
| 2007/0227538 A1 | 10/2007 | Scholler et al. |
| 2007/0227539 A1 | 10/2007 | Schwaibold et al. |
| 2007/0232951 A1 | 10/2007 | Euliano et al. |
| 2007/0267015 A1 | 11/2007 | Thoemmes et al. |
| 2007/0272243 A1 | 11/2007 | Sherman et al. |
| 2007/0277825 A1 | 12/2007 | Bordewick et al. |
| 2007/0284361 A1 | 12/2007 | Nadjafizadeh et al. |
| 2008/0000471 A1 | 1/2008 | Bolam et al. |
| 2008/0000475 A1 | 1/2008 | Hill |
| 2008/0000478 A1 | 1/2008 | Matthiessen et al. |
| 2008/0011294 A1 | 1/2008 | Heesch et al. |
| 2008/0017198 A1 | 1/2008 | Ivri |
| 2008/0029096 A1 | 2/2008 | Kollmeyer et al. |
| 2008/0033304 A1 | 2/2008 | Dalal et al. |
| 2008/0035146 A1 | 2/2008 | Crabb |
| 2008/0041382 A1 | 2/2008 | Matthews et al. |
| 2008/0053441 A1 | 3/2008 | Gottlib et al. |
| 2008/0072896 A1 | 3/2008 | Setzer |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0115786 A1 | 5/2008 | Sinderby et al. |
| 2008/0119753 A1 | 5/2008 | Ricciardelli et al. |
| 2008/0125828 A1 | 5/2008 | Ignagni et al. |
| 2008/0135044 A1 | 6/2008 | Freitag et al. |
| 2008/0139956 A1 | 6/2008 | Diong |
| 2008/0142019 A1 | 6/2008 | Lewis et al. |
| 2008/0156330 A1 | 7/2008 | Smith et al. |
| 2008/0163872 A1 | 7/2008 | Negele et al. |
| 2008/0178880 A1 | 7/2008 | Christopher |
| 2008/0178882 A1 | 7/2008 | Christopher et al. |
| 2008/0216833 A1 | 9/2008 | Pujol et al. |
| 2008/0251078 A1 | 10/2008 | Buckley et al. |
| 2008/0257337 A1 | 10/2008 | Denyer et al. |
| 2008/0275513 A1 | 11/2008 | Lattner et al. |
| 2008/0276940 A1 | 11/2008 | Fuhrman et al. |
| 2008/0281219 A1 | 11/2008 | Glickman et al. |
| 2008/0283060 A1 | 11/2008 | Bassin |
| 2008/0283061 A1 | 11/2008 | Tiedje |
| 2008/0294060 A1 | 11/2008 | Haro et al. |
| 2008/0295839 A1 | 12/2008 | Habashi |
| 2008/0295840 A1 | 12/2008 | Glaw |
| 2009/0013999 A1 | 1/2009 | Bassin |
| 2009/0056709 A1 | 3/2009 | Worsoff |
| 2009/0120439 A1 | 5/2009 | Goebel |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0293877 A1 * | 12/2009 | Blanch et al. ............ 128/204.23 |
| 2009/0301486 A1 | 12/2009 | Masic |
| 2009/0301487 A1 | 12/2009 | Masic |
| 2009/0301490 A1 | 12/2009 | Masic |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0116270 A1 | 5/2010 | Edwards et al. |
| 2010/0125227 A1 | 5/2010 | Bird |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0229863 A1 | 9/2010 | Enk |
| 2010/0236551 A1 | 9/2010 | Enk |
| 2010/0236555 A1 | 9/2010 | Jafari et al. |
| 2010/0242961 A1 | 9/2010 | Mougel et al. |
| 2010/0263669 A1 | 10/2010 | Bowsher |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0011403 A1 | 1/2011 | Hannah et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |

| | | |
|---|---|---|
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0138057 A1 | 6/2012 | Tham et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |

FOREIGN PATENT DOCUMENTS

| | | |
|---|---|---|
| EP | 1005830 A1 | 6/2000 |
| EP | 1103279 A2 | 5/2001 |
| EP | 996358 B1 | 1/2002 |
| EP | 1277435 B1 | 3/2006 |
| WO | 9706844 A1 | 2/1997 |
| WO | 9841147 A1 | 9/1998 |
| WO | 03/077747 A1 | 9/2003 |
| WO | 2004/002561 A2 | 1/2004 |
| WO | 2004/019766 A2 | 3/2004 |
| WO | 2006/079152 A1 | 8/2006 |
| WO | WO 2008/008659 | 1/2008 |
| WO | WO 2008/021222 | 2/2008 |
| WO | WO 2008/113752 | 9/2008 |
| WO | WO 2009/060330 | 5/2009 |

OTHER PUBLICATIONS

7200 Ventilatory System: Addendum/Errata. Nellcor Puritan Bennett, Part No. 4-023576-00, Rev. A, Apr. 1988, pp. 1-32. (32 pages).
800 Operator's and Technical Reference Manual. Series Ventilator System, Nellcor Puritan Bennett, Part No. 4-070088-00, Rev. L, Aug. 2010, pp. 1-476. (476 pages).
840 Operator's and Technical Reference Manual. Ventilator System, Nellcor Puritan Bennett, Part No. 4-075609-00, Rev. G, Oct. 2006, pp. 1-424. (424 pages).
International Search Report re: PCT/US2009/046409 mailed Sep. 29, 2009. (17 pages).
International Search Report re: PCT/US2009/046415 mailed Sep. 18, 2009. (3 pages).
International Search Report re: PCT/US2009/046412 mailed Sep. 21, 2009. (4 pages).
Reexamination # 90/011,363, which is a reexamination of U.S. Appl. No. 10/617,590, now US Patent No. 6,823,866, final correspondence date of Jul. 9, 2012, 274 pgs.
Reexamination # 90/011,362, which is a reexamination of US U.S. Appl. No. 10/997,533, now US Patent No. 7,000,612, final correspondence date of Jul. 2, 2012, 361 pgs.
Reexamination # 90/011,361, which is a reexamination of US U.S. Appl. No. 09/970,383, now US Patent No. 6,626,175, final correspondence date of Jun. 29, 2012, 565 pgs.
U.S. Appl. No. 12/479,230, Office Action mailed Apr. 23, 2012, 12 pgs.
U.S Appl. No. 12/479,249, Office Action mailed Apr. 23, 2012, 14 pgs.
U.S. Appl. No. 12/479,239, Office Action mailed Apr. 23, 2012, 8 pgs.
International Search Report in International Application PCT/US09/046418, mailed Sep. 29, 2009, 12 pgs.
Boitano, Louis J., "An Evaluation of Home Volume Ventilators That Support Open Circuit Mouthpiece Ventilation", Respiratory Care, Nov. 2005, vol. 50, No. 11, pp. 1457-1461.
U.S. Appl. No. 12/479,230, Office Action mailed Oct. 18, 2012, 11 pgs.
U.S. Appl. No. 12/479,249, Notice of Allowance mailed Nov. 2, 2012, 7 pgs.
U.S. Appl. No. 12/479,239, Office Action mailed Oct. 18, 2012, 10 pgs.
U.S. Appl. No. 12/479,230, Advisory Action mailed Dec. 28, 2012, 3 pgs.
U.S. Appl. No. 12/479,239, Notice of Allowance mailed Jan. 7, 2013, 6 pgs.
U.S. Appl. No. 13/076,184, Office Action mailed Jan. 31, 2013, 13 pgs.
U.S. Appl. No. 12/479,249, Notice of Allowance mailed Mar. 15, 2013, 7 pgs.
U.S. Appl. No. 12/479,239, Notice of Allowance mailed Mar. 15, 2013, 7pgs.
U.S. Appl. No. 12/980,583, Office Action mailed Jan. 28, 2013, 16 pgs.

* cited by examiner

SYSTEMS AND METHODS FOR VENTILATION IN PROPORTION TO PATIENT EFFORT

RELATED APPLICATIONS

This application claims the benefit of U.S. Provisional Application No. 61/059,599, filed Jun. 6, 2008, titled "Systems and Methods for Determining Patient Effort and/or Respiratory Parameters in a Ventilation System," the benefit of U.S. Provisional Application No. 61/101,575, filed Sep. 30, 2008, titled "Systems and Methods for Monitoring and Displaying Respiratory Information," and the benefit of U.S. Provisional Application No. 61/101,578, filed Sep. 30, 2008, also titled "Systems and Methods for Monitoring and Displaying Respiratory Information," and whereby the complete disclosure of each such application is hereby incorporated by reference.

BACKGROUND

The present invention is related to ventilators, and more particularly to systems and methods for identification of time dependent signals and/or respiratory parameters in a dynamic ventilation system.

Ventilators are designed to ventilate a patient's lungs with gas, and to thereby assist the patient when the patient's ability to breathe on their own is somehow impaired. Ventilation is achieved by providing a defined gas mixture to the patient according to a prescribed ventilation modality. As each patient may require a different ventilation strategy, modern ventilators can be customized for the particular needs of an individual patient.

Modern ventilators are dynamic systems whose dynamic behavior and outputs, such as pressures and flows delivered to the patient, are driven by input signals, such as gas flows. Proper operation of such ventilators relies on some understanding of a variety of respiratory parameters including the resistance of the patient airways and the compliance of the lung. These parameters may vary significantly from one ventilation system to another, and from one patient to another. In many cases, proper operation of a ventilation system is limited by the accuracy at which such parameters are defined or estimated.

Methods for identifying the ventilation parameters for a particular individual or a particular ventilation situation have been developed. Such methods can be divided into two different categories: static methods and dynamic methods. In static methods, respiratory parameters are typically estimated during short periods of induced equilibrium states (i.e., maneuvers) of the system using only a few measurements of quantities that are related to the estimated parameters. In contrast, dynamic methods operate to describe the dynamic behavior of the patient under ventilation, and are typically based on continuous or segmented continuous measurement of ventilator conditions. Historically, identifying respiratory parameters posed a challenge in the case of the ventilation system driven by unknown input signals. This is the case with the ventilation systems involving actively breathing patients and leaks, and many existing approaches fail to provide sufficiently accurate results because these signals driving the system typically cannot be measured but they must be accounted for in the identification algorithms. For example, various approaches for estimating patient breathing effort are inaccurate, and as such dynamic methods relying on an estimated patient effort are often inadequate.

In some cases, patient breathing effort has been estimated using the equation of motion, and relying exclusively on the measurement of gas flow in and out of the patient's lungs along with a pressure measurement. The reliability of such an approach is limited by the accuracy at which gas flow in and out of the patient's lungs may be measured. Such a measurement, however, is inherently inaccurate as it relies on a flow sensor at or near a tube inserted in the patient's trachea. The accuracy of the flow sensor is substantially reduced due to the humidity of gas exhaled from the lung. Further, such a flow sensor near the patient's trachea is often not available in existing ventilation systems.

Hence, there exists a need in the art for advanced ventilation systems, and methods for using such.

BRIEF SUMMARY

The present disclosure is related to ventilators, and more particularly to systems and methods for controlling the delivery of gas based at least in part on a patient's effort to breathe.

Some embodiments of the present disclosure provide ventilation systems that allow for ventilating a patient in proportion to the effort that the patient may be putting forth to breathe on their own. Some such systems include a processor capable of executing instructions available from a computer readable medium. The instructions provide for receiving a measured pressure value and receiving a net flow value. A patient effort value is calculated based on a relationship between the measured pressure value, the net flow value, and patient effort. A gas delivery metric is calculated, wherein the metric varies as a function of the patient effort value. The instructions are further executable to cause a gas to be delivered consistent with the gas delivery metric. In some instances, the gas delivery metric is selected from pressure and flow, where the flow may be patient lung flow, inlet gas flow, or other measureable or estimated flows, and the pressure may be lung pressure, pressure at a wye connection, or other measurable or estimated pressures.

In some instances of the aforementioned embodiments, the instructions are further executable to determine an inhalation phase based on the patient effort value. In some such instances, gas delivery is caused during the inhalation phase. In particular instances, the inhalation phase is indicated when the calculated patient effort value is greater than zero.

In various instances of the aforementioned embodiments, a first function of the patient effort value is a constant multiplier. In other instances, the first function of the patient effort value is a non-linear function. In yet other instances, the first function of the patient effort value is a time varying function.

In some instances, the patient effort value is further calculated by combining one or more intermediate values selected from an estimated normalized prediction error, a filtered pressure value, a regression vector, and a current estimate value of a parameter vector.

In some instances of the aforementioned embodiments, the relationship used to calculate a patient effort value is a parameterized system input to output relationship. In some instances, the parameterized system input to output relationship is the regression form:

$$z = \Theta^T \phi + \phi_d.$$

The parameterized input to output relationship may be derived from a transfer function, where in some instances the transfer function is derived from the model:

$$\begin{bmatrix} \dot{p}_Y \\ \dot{p}_L \end{bmatrix} = \begin{bmatrix} -\frac{1}{C_T R_P} & \frac{1}{C_T R_P} \\ \frac{1}{C_L R_P} & -\frac{1}{C_L R_P} \end{bmatrix} \begin{bmatrix} p_Y \\ p_L \end{bmatrix} + \begin{bmatrix} \frac{1}{C_T} & \frac{1}{C_T} & -\frac{1}{C_T} \\ 0 & 0 & 0 \end{bmatrix} \begin{bmatrix} q_{AIR} \\ q_{O2} \\ q_E \end{bmatrix} +$$

$$\begin{bmatrix} 0 & -\frac{1}{C_T} & 0 \\ 1 & 0 & -\frac{1}{C_T} \end{bmatrix} \begin{bmatrix} p_P \\ q_{Tleak} \\ q_{Pleak} \end{bmatrix}$$

Other embodiments of the present disclosure include methods for providing respiratory support. Such methods include measuring a pressure and providing a measured pressure, and measuring an inlet flow and an outlet flow, and providing a measured net flow. A relationship between a first value related to the measured pressure, a second value related to the measured net flow and a third value related to patient effort are used to calculate an estimate of patient effort. A gas is then supplied in proportion to the estimate of patient effort. In some instances, supplying the gas in proportion to the estimate of patient effort includes supplying the gas at some combination of a pressure in proportion to the estimate of patient effort and a flow in proportion to the estimate of patient effort. In some instances, the estimate of patient effort is based on a combination of one or more intermediate values derived from the measured pressure and measured net flow, with the intermediate values selected from an estimated normalized prediction error ($\epsilon$), a filtered pressure value (z), a regression vector ($\phi^T$), and a current estimated value of a parameter vector ($\Theta$).

In one or more instances of the aforementioned embodiments, the second value may be a filtered version of the measured net flow or the measured net flow. In some instances of the aforementioned embodiments, the first value may be a filtered version of the measured pressure or the measured pressure.

Yet other embodiments of the present invention provide ventilation systems that include a gas inlet, a gas outlet, a tube coupling the gas inlet and the gas outlet, a pressure sensor, and at least two flow sensors. The pressure sensor is operable to provide a measured pressure value indicating a pressure in the tube. One of the flow sensors is operable to provide an inlet flow value indicating a flow associated with the gas inlet, and the other of the flow sensors is operable to provide an outlet flow value indicating a flow associated with the gas outlet. A processor communicably coupled to a computer readable medium is included. The computer readable medium includes instructions executable by the processor to: receive a measured pressure value; receive a net flow value; calculate a patient effort value based on a relationship between patient effort, the measured pressure value and the net flow value; calculate a gas delivery metric that varies as a first function of the patient effort value; determine an inhalation phase based on the patient effort value, and cause a gas to be delivered consistent with the gas delivery metric. In some embodiments, the gas delivery metric is pressure and/or flow.

This summary provides only a general outline of some embodiments of the invention. Many other objects, features, advantages and other embodiments of the invention will become more fully apparent from the following detailed description, the appended claims and the accompanying drawings.

BRIEF DESCRIPTION OF THE DRAWINGS

A further understanding of the various embodiments of the present disclosure may be realized by reference to the figures which are described in remaining portions of the specification. In the figures, like reference numerals may be used throughout several of the figures to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION

Figure 1:
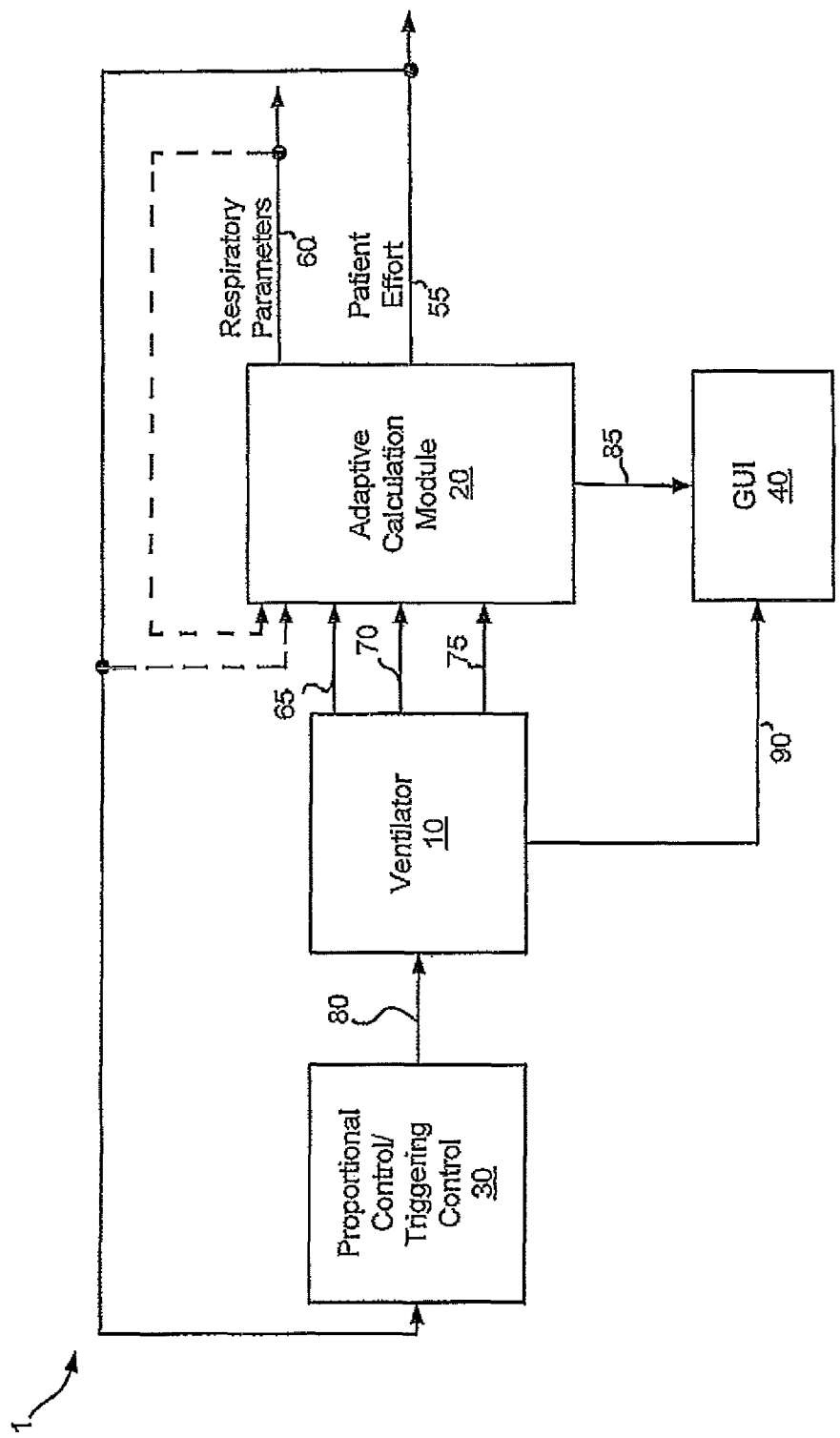
FIG. 1 depicts a ventilation system including, among other things, an adaptive calculation module capable of providing adaptively estimated respiratory parameters and patient effort in accordance with various embodiments of the present invention.

The present disclosure is related to ventilators, and more particularly to systems and methods for controlling the delivery of gas based on a patient's effort to breathe.

It is desirable to synchronize the onset and end of a ventilation cycle to effort a patient may be making to breathe on their own (i.e., patient effort). For example, it is desirable to have an accurate ventilator trigger, whereby the ventilator initiates a breath as soon as the patient attempts to inhale. Some ventilators use a pressure trigger which senses a change in ventilation circuit pressure caused by the patient attempting to inhale, while other ventilators use a flow trigger which senses a change in flow caused by the patient attempting to inhale. In either case, delays between the patient's effort and the ventilator response can occur due to a variety of reasons.

For example, a leak in the ventilation circuit may allow air to enter the circuit when the patient inhales. Since the entirety of the patient breath is not measured by a ventilator flow sensor, and the ventilator may be monitoring a change in flow to detect an inhalation (flow trigger), the ventilator may be delayed in initiating the breath. Some embodiments of the present invention facilitate improved synchronization through providing a reasonably accurate estimate of patient effort that may be used either alone or in relation to other signals to trigger the onset and end of a ventilation cycle. In one or more embodiments of the present invention, the estimated patient effort may be additionally used in relation to controlling proportional ventilation of a patient. Such proportional ventilation operates to deliver a gas to a patient in proportion to the patient's effort to receive such gas. In various embodiments of the present invention, the estimated patient effort and/or respiratory parameters may be used to drive a graphical display that may be used by a clinician for patient monitoring and/or diagnostic purposes.

Various embodiments of the present disclosure provide systems and methods for estimating of one or more respiratory parameters and at least one unmeasured input signal driving a ventilation system with a reasonable degree of accuracy. In some embodiments, at least one unmeasured input signal may be derived from measured input signals, such as a measured pressure and measured flow, and used to estimate the respiratory parameters. The unmeasured input signal may be, but is not limited to, patient effort and/or a derivative of patient effort, a ventilation system gas leak (i.e., a leak occurring in the tubing or patient interface connecting a ventilator to a patient), a patient gas leak (e.g., a leak in the patient's lung), and/or flow and pressure sensing errors. The respiratory parameters may include, but are not limited to, lung compliance ($C_L$), patient resistance ($R_P$), and tubing compliance ($C_T$). In some cases, estimation of both respiratory parameters and the unmeasured input signal(s) is simultaneous. In some embodiments, the unmeasured input signal has a strong correlation to patient effort, and therefore can be used as a surrogate for patient effort in subsequent ventilator actions. In other embodiments, methods of the present invention allow the respiratory parameters to be continuously provided. In this manner, patient effort may be determined, as well as respiratory or ventilation system parameters such as lung compliance, patient resistance, leak, etc.

In some embodiments of the present invention, a relationship between measurable pressure, measurable flow and an unknown patient effort is exploited to provide a continuous estimate of patient effort along with a variety of respiratory parameters. In particular instances, the relationship is defined as a transfer function relating, inter alia, measured pressure, measured flow and patient effort. In such cases, the transfer function may be reduced using linear regression techniques to yield one or more interim values that may in turn be used to estimate patient effort. In an embodiment, ongoing inputs of measured pressure and measured flow are plugged into the transfer function to estimate patient effort and, as needed, one or more respiratory parameters. In another embodiment, the estimate of patient effort may be used recursively to derive a more accurate estimate of patient effort during succeeding calculation periods. Thus, through use of recursion, the accuracy of an estimated patient effort value may be continuously improved.

In some cases, the measured flow is a net flow value that combines a net flow of gas out of the system with a net flow of gas into the system. In one particular case, the net flow of gas into the system includes a flow of Oxygen combined with a flow of Air into the system. Such flows are reasonably easy to measure, and are not subject to the inaccuracies that often attend the measurement of gas flow near the lung.

In some cases, a patient effort signal or some proxy thereof calculated as described above may be used to trigger a ventilation cycle. Use of such signals can allow a ventilation system to more accurately synchronize mechanical ventilation with the efforts being made by a patient to breathe on their own.

Of note, the respiratory parameters and the derivative of patient effort may be inputs to the same model, and may be calculated using interdependent equations derived from that same model. As the values calculated from some of the interdependent equations are used as inputs to other interdependent equations, they may be generically referred to as interim values. As used herein, the phrase "interim value" is used in its broadest sense to mean a value derived from one equation that is used as an input to another equation. It will be noted based on reading this disclosure that a variety of interim values may be utilized in relation to the various embodiments of the present invention.

Turning to FIG. 1, a ventilation system 1 is shown in accordance with various embodiments of the present invention. Ventilation system 1 includes a ventilator 10, an adaptive calculation module 20, a graphical user interface 40, and a proportional and triggering control module 30. Ventilator 10 may be any ventilator known in the art that is capable of providing a measured pressure 65, a measured inlet flow 70 and a measured outlet flow 75. Adaptive calculation module 20 receives pressure 65, inlet flow 70 and outlet flow 75 and calculates an estimated patient effort 55 and estimated respiratory parameters 60. Patient effort 55 may be patient effort itself or some signal that is strongly correlated to patient effort. Signals correlated to patient effort are more fully discussed below. Respiratory parameters 60 may include a variety of parameters that are more fully described below. In an embodiment, the calculations performed by adaptive calculation module 20 may be adaptive in nature relying on previous interim values to generate updated respiratory parameters 60 and patient effort 55 estimates. In some embodiments, such interim values may include the patient effort 55 and/or the respiratory parameter estimates 60 as shown by dashed lines in FIG. 1. Alternatively (not shown), the previous interim values used by adaptive calculation module 20 may be composite parameters that do not directly correspond to any identifiable respiratory parameter (such as, for example, the covariance matrix and parameter vector discussed in greater detail below).

In the embodiment illustrated, patient effort 55 is provided to proportional and triggering control module 30. Based on patient effort 55, proportional and triggering control module 30 generates one or more control signals 80 that are provided to ventilator 10. In some embodiments, control signals 80 control the timing of gas delivery to a patient. In various embodiments, control signals 80 control the amount of gas to be delivered to a patient, where the amount of gas is in proportion to patient effort 55.

Ventilator 10 provides control signals 90 that drive graphical user interface 40. Graphical user interface 40 may be included as part of ventilator 10 to allow for interaction with a user including, but not limited to, receiving user commands and/or displaying data relevant to ventilator operation. In some embodiments, ventilator 10 may direct graphical user interface 40 to display information 85 provided by adaptive calculation module 20. Such information may include, but is not limited to, respiratory parameters 60 and/or patient effort 55 as is more fully discussed below.

Figure 2:
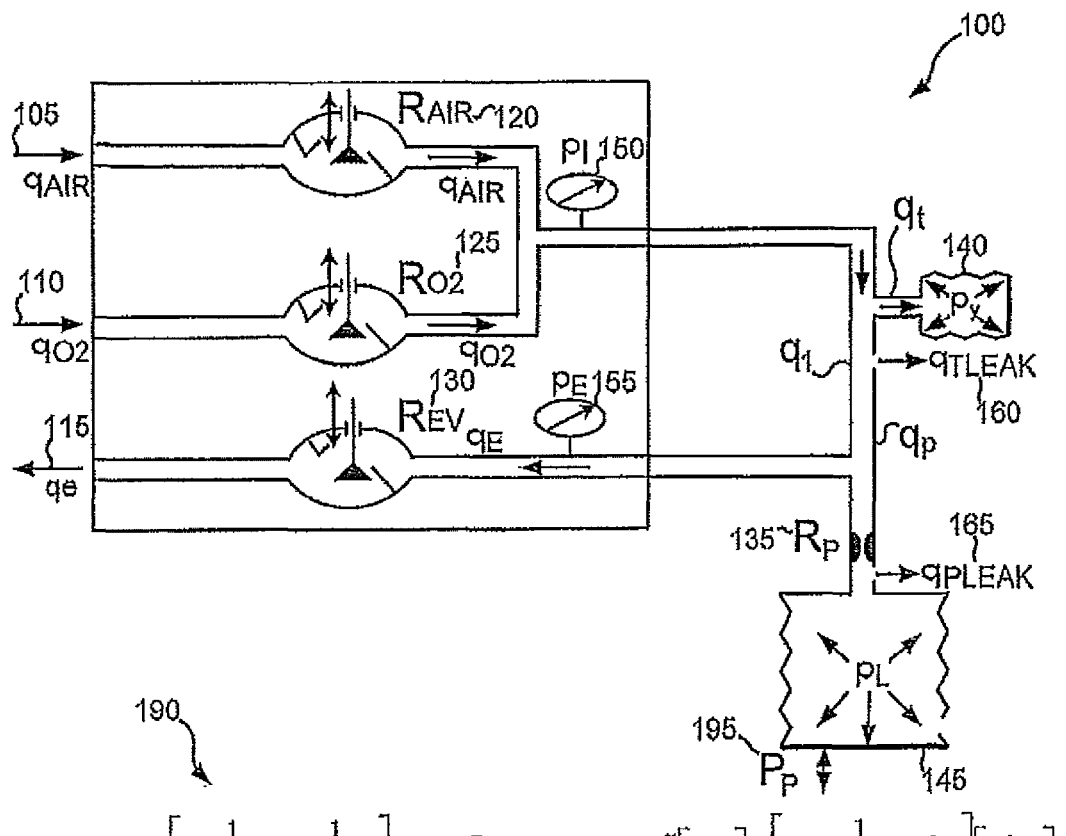
FIG. 2 shows a patient ventilator system and associated parameterized model that may be used for determining patient effort in accordance with some embodiments of the present invention.

Various embodiments of the present invention utilize a parameterized dynamic model of a patient ventilator system to determine patient effort. A model of a ventilator system 100 is depicted in FIG. 2. Ventilator system 100 includes an inlet air flow 105 ($q_{AIR}$), an inlet Oxygen flow 110 ($q_{O2}$), and an outlet gas flow 115 ($q_E$). It should be noted that while ventilator system 100 shows two gas sources, Air and Oxygen, more or fewer inlet gas sources may be used in relation to different embodiments of the present invention. For example, it may be that only an Air source is used, or that in addition to the inlet Air source and the inlet Oxygen source, a Helium and/or Heliox source may be included. Based on the disclosure provided herein, one of ordinary skill in the art will recognize a variety of other gas sources that may be used in relation to different embodiments of the present invention.

Tubing, flow valves, and/or pressure monitors included in the system introduce some resistance to gas flow in ventilator system 100. In particular, an air resistance 120 ($R_{air}$), an Oxygen resistance 125 ($R_{O2}$), an exhalation resistance 130 ($R_{EV}$), and a patient resistance 135 ($R_P$) (i.e., some combination of trachea resistance and resistance in an endotracheal tube) are possible. A pressure sensor 150 measures the pressure ($p_I$) at the inlet at a location where the air flow and Oxygen flow is combined, and a pressure sensor 155 measures the pressure ($p_E$) in an exhalation output. It should be noted that pressure sensor 150 may be replaced by individual pressure sensors associated with respective inlet lines. The pressure ($p_Y$) at a location where inlet and outlet gases combine is represented as a baffles 140 (e.g., wye gas pressure), and the pressure ($p_L$) in the patient's lungs is represented by another baffles. In some embodiments of the present invention, $p_Y$ is determined though use of a pressure measurement device mounted at or near the particular location corresponding to the pressure. In other embodiments of the present invention, $p_Y$ is set equal to either $p_I$ or $p_E$, while in other embodiments of the present invention, $p_Y$ is set to the average of $p_I$ and $p_E$. In any of the aforementioned three cases, $p_Y$ is considered to be "directly measured" as it is either a measurement or is an average of other direct measurements. A gas flow associated with a leakage 160 ($q_{Tleak}$) in the tubing, and a gas flow associated with a leakage 165 ($q_{Pleak}$) in the patient are also identified. A patient effort value 195 ($p_P$) is shown as a force interacting with the force of moving gas in and out of a patient's lung.

Various equations may be used to describe the operation of ventilator system 100. For example, using the principle of conservation of mass, the various flow values (i.e., $q_{AIR}$, $q_{O2}$, $q_T$, $q_{Tleak}$, $q_P$, $q_{Pleak}$, $q_{LUNG}$, $q_1$) may be combined to yield the following three equations:

$$q_{LUNG} = q_P - q_{Pleak};$$

$$q_1 - q_P - q_E = 0;\text{ and}$$

$$q_{AIR} + q_{O2} = q_1 + q_{Tleak} + q_T.$$

Further, using the principle of equilibrium of forces, the pressures $p_Y$, $p_L$ and $p_P$, and flows $q_T$ and $q_L$ can be combined in the following relationships:

$$p_Y = \frac{1}{C_T}\int q_T dt,\text{ or }\dot{p}_Y = \frac{1}{C_T}q_T;\text{ and}$$

$$p_P - p_L = \frac{1}{C_L}\int q_L dt,\text{ or }\dot{p}_L = \dot{p}_P - \frac{1}{C_L}q_L.$$

Finally, the relationship between pressure and flow can be used to derive the following equation based on ventilator system 100:

$$p_Y - p_L = R_P \cdot q_P.$$

By algebraically manipulating the aforementioned equations derived from ventilator system 100 and recasting the equations in a matrix form, the following parameterized model 190 is developed to characterize the operation of ventilator system 100 of FIG. 2:

$$\begin{bmatrix}\dot{p}_Y\\\dot{p}_L\end{bmatrix} = \begin{bmatrix}-\frac{1}{C_T R_P} & \frac{1}{C_T R_P}\\\frac{1}{C_L R_P} & -\frac{1}{C_L R_P}\end{bmatrix}\begin{bmatrix}p_Y\\p_L\end{bmatrix} + \begin{bmatrix}\frac{1}{C_T} & \frac{1}{C_T} & -\frac{1}{C_T}\\0 & 0 & 0\end{bmatrix}\begin{bmatrix}q_{AIR}\\q_{O2}\\q_E\end{bmatrix} +$$

$$\begin{bmatrix}0 & -\frac{1}{C_T} & 0\\1 & 0 & -\frac{1}{C_T}\end{bmatrix}\begin{bmatrix}\dot{p}_P\\q_{Tleak}\\q_{Pleak}\end{bmatrix},$$

where $\dot{p}_Y$ is the first derivative of the pressure measured at the tubing branch, $\dot{p}_L$ is the first derivative of the pressure in the patient's lung, $\dot{p}_P$ is the first derivative of the patient effort, $C_T$ represents tubing compliance, and $C_L$ represents lung compliance. It should be noted that where more or fewer inlet gases are utilized, that parameterized model 190 may be modified to account for the different gases in accordance with other embodiments of the present invention.

Various embodiments of the present invention utilize parameterized model 190 to determine patient effort, $p_P$. In different embodiments of the present invention, assumptions may be made to simplify the calculation. In one particular embodiment of the present invention, leakage 160 may be assumed to exhibit the following linear relationship between the tubing leak flow and the pressure drop across an opening:

$$q_{Tleak} = \frac{1}{R_{LEAK}}p_y = \lambda_{LEAK}p_y.$$

It should be noted that in other embodiments of the present invention, other assumptions about the relationship between the tubing leak flow and the pressure drop across an opening may be used. Relying on the aforementioned linear assumption for the tubing leak flow, parameterized model 190 may be reduced to the following model:

$$\begin{bmatrix}\dot{p}_Y\\\dot{p}_L\end{bmatrix} = \begin{bmatrix}-\frac{1}{C_T R_P} - \frac{\lambda_{Tleak}}{C_T} & \frac{1}{C_T R_P}\\\frac{1}{C_L R_P} & -\frac{1}{C_L R_P}\end{bmatrix}\begin{bmatrix}p_Y\\p_L\end{bmatrix} +$$

$$\begin{bmatrix}\frac{1}{C_T} & \frac{1}{C_T} & -\frac{1}{C_T}\\0 & 0 & 0\end{bmatrix}\begin{bmatrix}q_{AIR}\\q_{O2}\\q_E\end{bmatrix} + \begin{bmatrix}0 & 0\\1 & -\frac{1}{C_L}\end{bmatrix}\begin{bmatrix}\dot{p}_P\\q_{Pleak}\end{bmatrix}.$$

Based on the aforementioned parameterized model, the transfer function for $p_Y$ is defined as follows:

$$p_Y(s) = \frac{b_q(s)}{a(s)}(q_{AIR}(s) + q_{O2}(s) - q_E(s)) + \frac{b_{Pp}(s)}{a(s)}\dot{p}_P(s) + \frac{b_{Pleak}(s)}{a(s)}$$

-continued $$q_{Pleak}(s) = \frac{b_q(s)}{a(s)} q_N(s) + \frac{b_{Pp}(s)}{a(s)} \dot{p}_P(s) + \frac{b_{Pleak}(s)}{a(s)} q_{Pleak}(s),$$

where the instantaneous sum of each of the measured flows (e.g., $q_{AIR}+q_{O2}-q_E$) is denoted $q_N$ for net flow.

$$\frac{b_q(s)}{a(s)} q_N(s)$$

represents a transfer function from the net flow ($q_N$) to the output ($p_Y$), $$\frac{b_{Pp}(s)}{a(s)} \dot{p}_P(s)$$

represents a transfer function from the derivative of patient effort ($\dot{p}_P$) to the output ($p_Y$), and $$\frac{b_{Pleak}(s)}{a(s)} q_{Pleak}(s)$$

represents a transfer function from patient leakage ($q_{Pleak}$) to the output ($p_Y$). It should be noted that the first term in the preceding transfer function (i.e., the $q_N$ term) is a transfer function related to a known, measured value, and the second term in the preceding transfer function (i.e., the $p_p$ term) is a transfer function related to an unknown, adaptively estimated value. In some embodiments of the present invention, the third term (i.e., the $q_{Pleak}$ term is assumed to be zero for the sake of simplification. Again, using the above mentioned parameterized model, the relationships between the transfer function coefficients and the system parameters are as follow:

$$a(s) = s^2 + \frac{C_L + C_T + C_L R_P \lambda_{Tleak}}{C_L C_T R_P} s + \frac{\lambda_{Tleak}}{C_L C_T R_P} = s^2 + a_1 s + a_0,$$

with $$a_1 = \frac{C_L + C_T + C_L R_P \lambda_{Tleak}}{C_L C_T R_P}, \quad a_0 = \frac{\lambda_{Tleak}}{C_L C_T R_P}$$

$$b_q(s) = \frac{1}{C_T} s + \frac{1}{C_L C_T R_P} = b_{q1} s + b_{q0},$$

with $$b_{q1} = \frac{1}{C_T}, \quad b_{q0} = \frac{1}{C_L C_T R_P}$$

$$b_{Pp}(s) = \frac{1}{C_T R_P} = b_{Pp0}$$

$$b_{Pleak}(s) = -\frac{1}{C_L C_T R} = b_{Pleak0}$$

From the forgoing, it is possible to derive a parameterized output model in a linear regression form. A first step in defining the parameterized linear regression output model includes defining an unknown parameter vector such as the following:

$$\Theta^T = [a_0 \ a_1 \ b_{q0} \ b_{q1}].$$

From the unknown parameter model, once estimated, all lumped parameters of ventilator system 100 (e.g., $C_T$, $C_L$, $R_P$, and $\lambda_{LEAK}$) may be recovered. Through algebraic manipulation of the transfer function for $p_Y$ may be represented as:

$$p_Y(s) \frac{s^2}{\Lambda(s)} = -p_Y(s) \frac{(a_1 s + a_0)}{\Lambda(s)} + b_q(s) \frac{q_N(s)}{\Lambda(s)} + b_{Pp}(s) \frac{\dot{p}_P(s)}{\Lambda(s)} + b_{Pleak}(s) \frac{q_{Pleak}(s)}{\Lambda(s)}.$$

In this case, the pressure $$p_Y(s) \frac{s^2}{\Lambda(s)}$$

represents pressure $p_Y(s)$ after filtering through a proper filter, $$\frac{s^2}{\Lambda(s)}.$$

Such a proper-filter relies on a polynomial $\Lambda(s)$ that is the same or of higher order than $s^2$ (e.g., $s^2$, $s^3$, $s^4$ . . . ). By assuming that patient leakage ($q_{Pleak}$) is zero, a compact linear regression form of the input to output relationship corresponding to parameterized model 190 of ventilation system 100 is represented as:

$$z = \Theta^T \varphi + \varphi_d$$

$$z = p_Y(s) \frac{s^2}{\Lambda(s)}$$

$$\Theta^T = [a_0 \ a_1 \ b_{q0} \ b_{q1}]$$

$$\varphi^T = \left[ -\frac{p_Y(s)}{\Lambda(s)} \ -\frac{p_Y(s)s}{\Lambda(s)} \ \frac{q_N(s)}{\Lambda(s)} \ \frac{q_N(s)s}{\Lambda(s)} \right]$$

$$\varphi_d = b_{Pp}(s) \frac{\dot{p}_P(s)}{\Lambda(s)}$$

where z is the output pressure value, $\phi^T$ is the regression vector representing a collection of known signals, and $\phi_d$ is filtered patient effort.

In this case, use of standard linear regression to estimate the system parameters $\Theta^T = [a_0 \ a_1 \ b_{q0} \ b_{q1}]$ is not possible as $\phi_d$ is unknown. By inspecting the unknown term $$\varphi_d = b_{Pp}(s) \frac{\dot{p}_P(s)}{\Lambda(s)},$$

and understanding that the derivative of patient effort ($\dot{p}_P$) is a bounded signal, that the filter ($\Lambda(s)$) is a stable polynomial, and $$\frac{b_{Pp}(s)}{\Lambda(s)}$$

is a proper linear filter, it is apparent that the unknown filtered patient effort (i.e., $\phi_d$) is a smooth signal. Based on this understanding, the value of the unknown filtered patient effort at any time t can be approximated by its value at the time t−dt, where dt represents an infinitesimal or finite, but small amount of time:

$$\phi_d \approx \phi_d e^{-s \cdot dt} = e^{-s \cdot dt}(z - \Theta^T \phi).$$

In some embodiments of the present invention, dt is five milliseconds or less. The aforementioned approximation represents a reasonable guess, or prediction, of the unknown filtered patient effort signal at time t that may be used in calculating respiratory parameters, and thereafter in calculating patient effort. This reasonable guess can be used to determine the predicted value ($\hat{z}$) of the system output (z) can be defined in accordance with the following equation:

$$\hat{z} = \Theta^T \phi + e^{-s \cdot dt}(z - \Theta^T \phi) = \Theta^T(\phi - e^{-s \cdot dt}\phi) + e^{-s \cdot dt}z.$$

From this definition, the parametric identification problem can be solved through formulation of the following problem: Given $\phi(t), z(t)$, find $$\Theta = \arg\left[\min_{\Theta} J(z - \hat{z})\right],$$

where $J()$ is a convex (e.g., $(\ )^2$) function of $\Theta$. From this point, one of a number of mathematical solutions may be applied to resolve the problem. As one example, a modified recursive least squares method may be used. More detail related to a non-modified mathematical implementation of such an approach is more fully described in one or both of (1) Lennart Ljung, "System Identification, Theory for the User", Second Edition, Prentice Hall, 1999 (ISBN 0-13-656695-2) and (2) Petros Ioannou and Jing Sun, Robust Adaptive Control, Prentice Hall, 1995 (ISBN 9780134391007). Both of the aforementioned references are incorporated herein by reference for all purposes.

In implementing a modified recursive least squares method, a prediction error ($\epsilon$) is first normalized and signals are adopted for the normalized signals as set forth in the following equation:

$$\varepsilon = \frac{z - \hat{z}(t)}{m^2}$$
$$= \frac{z - \Theta^T(\varphi - e^{-s \cdot dt}\varphi) - e^{-s \cdot dt}z}{m^2}$$
$$= \frac{z(1 - e^{-s \cdot dt}) - \Theta^T \varphi(1 - e^{-s \cdot dt})}{m^2}$$
$$= \frac{\tilde{z} - \Theta^T \tilde{\varphi}}{m^2}$$

$$\tilde{z} = z(1 - e^{-s \cdot dt})$$
$$\tilde{\varphi} = \varphi(1 - e^{-s \cdot dt})$$
$$m^2 = 1 + \tilde{\varphi}^T \tilde{\varphi}$$

where $\epsilon$ is the normalized prediction error, $\tilde{z}$ and $\tilde{\phi}$ are the differences of the output and regressor respectively corresponding to the time interval dt, and m is the normalization signal. In addition, a modified function $J()$ (referred to as a cost function) is adopted in accordance with the following equation:

$$J(\Theta(t)) = \frac{1}{2}\int_0^t e^{-\beta(t-\tau)}\frac{(\tilde{z} - \Theta^T\tilde{\varphi})^2}{m^2}d\tau + \frac{1}{2}e^{-\beta t}(\Theta - \Theta_0)^T Q_0(\Theta - \Theta_0),$$

where $\beta > 0$ and $Q_0 \geq 0$ are referred to as a forgetting factor and a penalty matrix. Based on this, the following stationary conditions must be met at the solution $\Theta$:

$$\frac{\partial}{\partial \Theta}J(\Theta(t)) = e^{-\beta t}Q_0(\Theta - \Theta_0) - \int_0^t e^{-\beta(t-\tau)}\frac{\tilde{z}\tilde{\varphi}}{m^2}d\tau +$$
$$\int_0^t e^{-\beta(t-\tau)}\frac{\tilde{\varphi}\tilde{\varphi}^T}{m^2}d\tau \Theta =$$
$$= \left[e^{-\beta t}Q_0 + \int_0^t e^{-\beta(t-\tau)}\frac{\tilde{\varphi}\tilde{\varphi}^T}{m^2}d\tau\right]\Theta -$$
$$\left[e^{-\beta t}Q_0\Theta_0 + \int_0^t e^{-\beta(t-\tau)}\frac{\tilde{z}\tilde{\varphi}}{m^2}d\tau\right] =$$
$$= P^{-1}\Theta - \left[e^{-\beta t}Q_0\Theta_0 + \int_0^t e^{-\beta(t-\tau)}\frac{\tilde{z}\tilde{\varphi}}{m^2}d\tau\right]$$
$$= 0$$

Thus, $\Theta$ can be found non-recursively as:

$$\Theta = P\left[e^{-\beta t}Q_0(\Theta - \Theta_0) + \int_0^t e^{-\beta(t-\tau)}\frac{\tilde{z}\tilde{\varphi}}{m^2}d\tau\right],$$

where:

$$P = \left[e^{-\beta t}Q_0 + \int_0^t e^{-\beta(t-\tau)}\frac{\tilde{\varphi}\tilde{\varphi}^T}{m^2}d\tau\right]^{-1}.$$

Matrix P and vector $\Theta$ satisfy the following two differential equations which complete the definition of the recursive algorithm that can be used to solve the parameter identification problem:

$$\dot{P} = \beta P - P\frac{\tilde{\varphi}\tilde{\varphi}^T}{m^2}P, \ P(0) = P_0 = Q_0^{-1}$$
$$\dot{\Theta} = P\varepsilon\tilde{\varphi},$$

where $\epsilon$ is the normalized error or difference between the last measured values and current measured values.

In the following discussion, methods are described that can be used to indirectly estimate a current value of patient effort in real time. In addition, it is demonstrated how various combinations of the above mentioned interim values (e.g., signals internal the transfer function) explained above possess a significant level of correlation with the unmeasured patient effort. Because of the correlation, the interim values may be used to characterize patient effort with a reasonable degree of accuracy.

From the relationships established above, it is clear that:

$$\varphi_d = (z - \Theta^T\varphi) = b_{Pp}(s)\frac{p_P(s)}{\Lambda(s)}.$$

By choosing an appropriate filter, $$\frac{1}{\Pi(s)},$$

that yields $$\frac{\Lambda(s)}{b_{P_p}(s)} \frac{1}{\Pi(s)},$$

an estimate of the derivative of patient effort ($\hat{\dot{p}}_P$) of the real derivative of patient effort ($\dot{p}_P$) can be computed as follows:

$$\hat{\dot{p}}_P(s) = (z - \Theta^T \varphi) \frac{\Lambda(s)}{b_{P_p}(s)} \frac{1}{\Pi(s)}.$$

Based on the following equation, it is apparent that a prediction error signal, $z - \hat{z}$, is correlated with the patient effort signal, $\dot{p}_P$, and the filtered version thereof, $\phi_d$:

$$\begin{aligned}
z - \hat{z} &= \Theta^T \varphi + \varphi_d - (\Theta^T \varphi + e^{-sdt}(z - \Theta^T \varphi)) \\
&= \varphi_d - e^{-sdt} \varphi_d \\
&= d \frac{\varphi_d(t - dt)}{dt} dt.
\end{aligned}$$

Using the transfer function defined above and the current estimate of the parameter vector $\Theta$, a prediction ($\hat{p}_y$) of the current pressure in the tubing ($p_y$) is represented by the following equation:

$$\hat{p}_Y(s, \Theta) = \frac{b_q(s, \Theta)}{a(s, \Theta)} q_N(s).$$

From this, the prediction error may be described by the following equation:

$$p_y - \hat{p}_y = \frac{b_{P_p}(s)}{a(s)} \dot{p}_P(s),$$

Which is a filtered version of the derivative of patient effort ($\dot{p}_P$). Moreover, if the ventilation system is characterized by the absence of tubing leaks (i.e., assume $\lambda_{LEAK}=0$), then the prediction error, $p_y - \hat{p}_y$, resembles the patient effort signal ($\dot{p}_P$) as the transfer function $$\frac{b_{P_p}(s)}{a(s)}$$

is an integration function.

Figure 3:
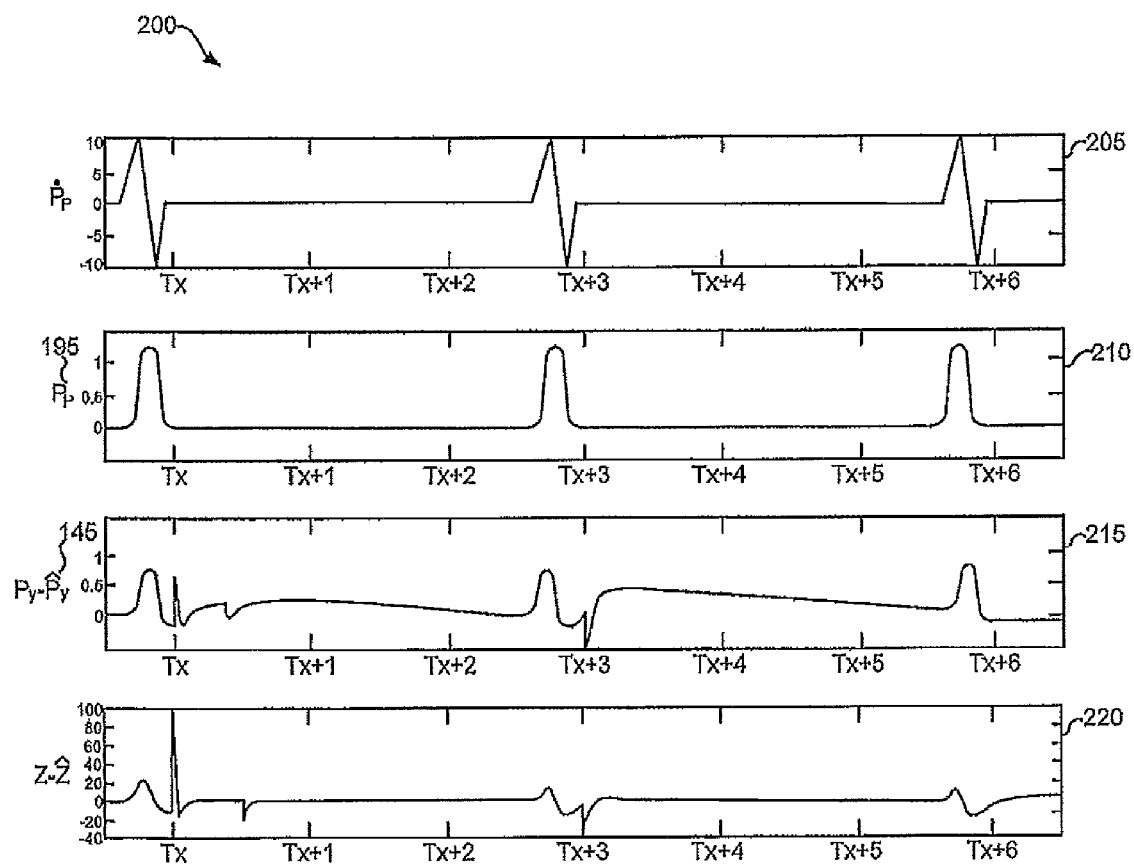
FIG. 3 provides a graphical example of patient effort correlated to other signals that is achievable through implementation of a particular embodiment of the present invention.

The aforementioned equations describe relationships between patient effort (i.e., $p_P$ and/or $\dot{p}_P$), and accurately obtainable flow and pressure measurements. FIG. 3 graphically depicts the exemplary correlation between patient effort (i.e., $p_P$ and/or $\dot{p}_P$) and exemplary signals internal to the previously described algorithm. As shown, a timing diagram 210 depicts patient effort ($p_P$) as a function of time. A timing diagram 205 depicts the first derivative of patient effort ($\dot{p}_P$) as a function of time. A timing diagram 215 depicts $p_y - \hat{p}_y$ and a timing diagram 220 depicts $z - \hat{z}$. The magnitude of each of $p_P$, $\dot{p}_P$, $p_y - \hat{p}_y$, and $z - \hat{z}$ is represented in centimeters of $H_2O$. As would be expected based on the analysis provided above, there is a strong correlation between patient effort ($p_P$) depicted in diagram 210 and the signal $p_y - \hat{p}_y$ depicted in diagram 215. Similarly, diagrams 205 and 220 demonstrate a strong correlation between the first derivative of the patient effort, $\dot{p}_P$, and the signal $z - \hat{z}$. Thus, the reconstructed signals can be used to predict the otherwise unknown signals $\dot{p}_P$ and $p_P$. It should be noted that the results are merely exemplary, and that based on the disclosure provided herein, one of ordinary skill in the art will recognize a variety of different signals and their delayed versions that may be achieved through use of different embodiments of the present invention to characterize the unknown patient effort signals and the derivatives thereof.

Figure 4:
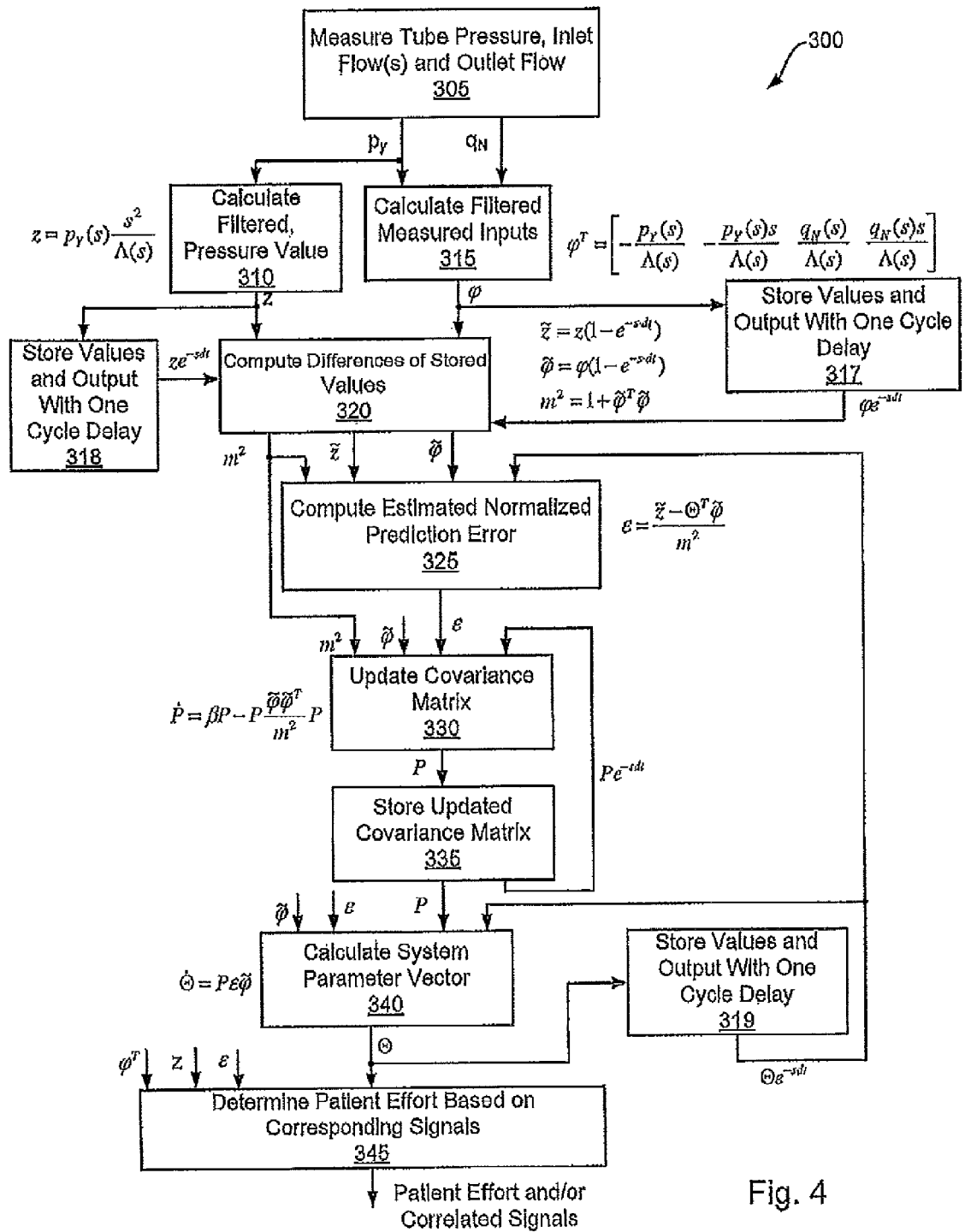
FIG. 4 is a flow diagram depicting a method in accordance with some embodiments of the present invention for determining patient effort; for determining patient effort in accordance with various embodiments of the present invention.

Turning to FIG. 4, a flow diagram 300 depicts a method in accordance with some embodiments of the present invention for determining patient effort. A ventilator system is provided that includes a ventilator that is coupled to a subject using various tubing. The ventilator receives one or more inlet gas flows and includes an outlet gas flow in addition to an inlet/outlet to the subject. Following flow diagram 300, pressure in the tubing ($p_y$) is measured along with the inlet flow(s) and the outlet flow to generate a net flow ($q_n$) (block 305). The pressure value ($p_y$) is filtered and provided as an output (z) (block 310), and the pressure ($p_y$) and net flow value ($q_n$) are filtered and combined in a regression vector ($\phi^T$) (block 315). Differences and/or derivatives of the aforementioned values (i.e., z and $\phi^T$) are calculated to generate outputs $m^2$, $\tilde{z}$ and $\tilde{\phi}$ (block 320). In addition, time delayed versions of z (i.e., $ze^{-sdt}$) and $\tilde{\phi}$ (i.e., $\tilde{\phi} e^{-sdt}$) are created (blocks 317, 318). $m^2$, $\tilde{z}$, $\tilde{\phi}$ and $\Theta^T$ are combined to generate an estimated normalized prediction error ($\epsilon$) (block 325); and $m^2$, $\tilde{\phi}$ and $\epsilon$ are used along with a previously computed covariance matrix ($P_0$) to calculate an updated covariance matrix (P) (block 330). The newly calculated covariance matrix (P) is stored and maintained as the previously computed covariance ($P_0$) for use in later updating of the covariance matrix (block 335). The updated covariance matrix (P) is used along with the previously computed $\epsilon$ and $\tilde{\phi}$ values to calculate an updated system parameter vector ($\Theta$) (block 340). In addition, a time delayed version of $\Theta$ (i.e., $\Theta e^{-sdt}$) generated (block 319). As discussed above, the system parameter vector ($\Theta$) incorporates various system parameters including, for example, tubing compliance ($C_T$), lung compliance ($C_L$), lumped resistance ($R_P$), and leakage ($\lambda_{LEAK}$).

During the above mentioned processing (blocks 305-340), various of the interim values may be used either separately or in combination to estimate patient effort (block 345). For example, as depicted in FIG. 3 above, z correlates to patient effort. Further, as z may be calculated using other constituent elements, the constituent elements may also be used to estimate patient effort. Based on the disclosure provided herein, one of ordinary skill in the art will recognize other uses of the constituent elements to predict patient effort.

Figure 5:
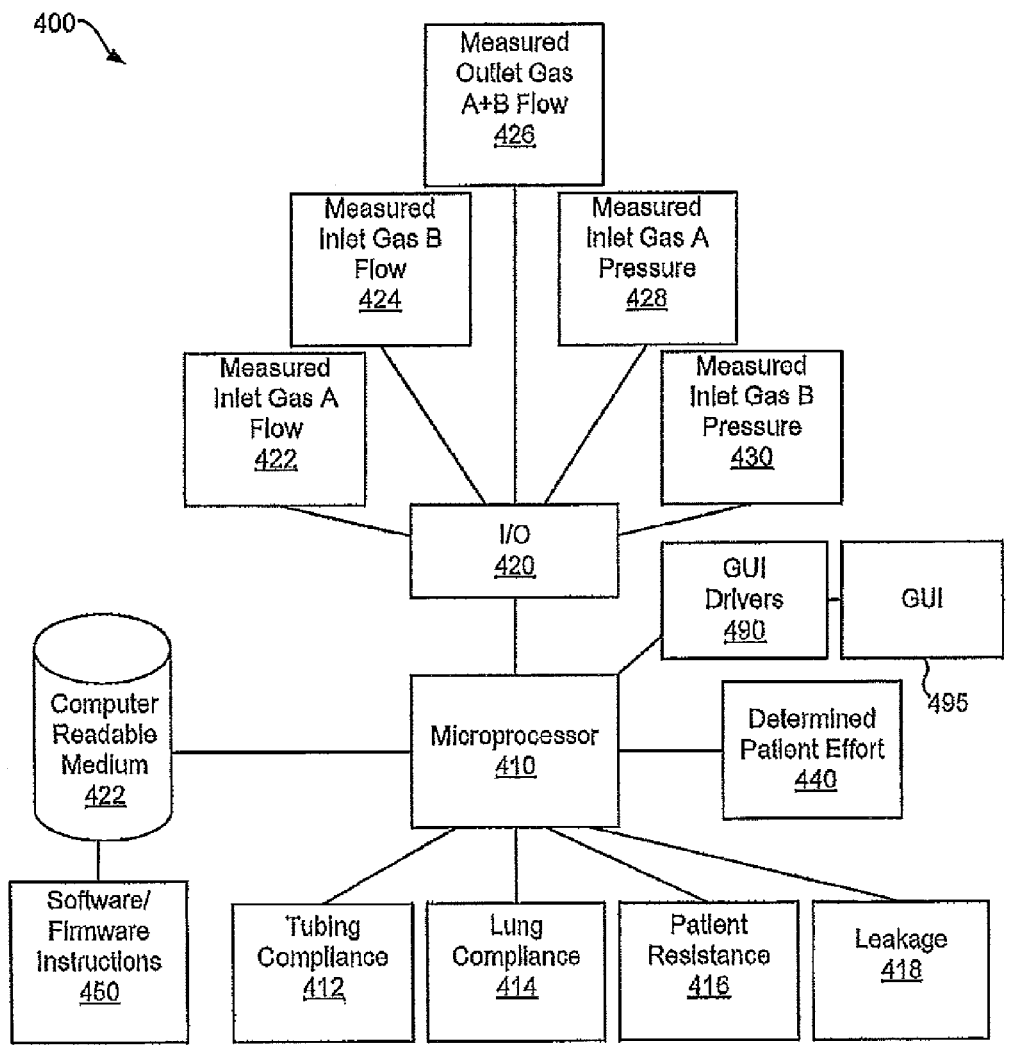

Turning to FIG. 5, a microprocessor based system 400 for determining patient effort is depicted in accordance with various embodiments of the present invention. System 400 includes a microprocessor 410 communicably coupled to a computer readable medium 460. Microprocessor 410 may be any processor known in the art that is capable of receiving various input values, and executing software or firmware instructions to provide an output based on the input values. Computer readable medium 460 may be any media capable of storing instructions that are executable by microprocessor 410. Based on the disclosure provided herein, one of ordinary skill in the art will recognize a variety of processors that may be used in relation to different embodiments of the present invention. As just some examples, computer readable medium 460 may be a hard disk drive, a tape drive, a portable solid state memory, a CD ROM, a RAM, combinations of the aforementioned, or the like. Based on the disclosure provided herein, one of ordinary skill in the art will recognize a variety of media and combinations of the media that may be used in relation to different embodiments of the present invention.

Instructions 450 when executed cause microprocessor 410 to receive various I/O via an I/O interface 420. The received I/O include measured inlet gas flows 422, 424, and a measured outlet gas flow 426. In some cases, the measured inlet gas flows measure the flow of Air and Oxygen, respectively. It should be noted that more or fewer than two inlet gas flows may be measured depending upon the particular embodiment of the present invention. Outlet gas flow 426 measures the gas flow being exhaled from system 400. Further, the received I/O include measured inlet gas pressures 428, 430 associated with the respective inlet gas flows 422, 424. It should be noted that where there are more or fewer inlet gas flows that the I/O may include more or fewer measured gas pressure inputs. Further, in some embodiments of the present invention, a single gas pressure input may be provided in place of inlet gas pressures 428, 430 where a single gas pressure sensor is placed in system 400 at a location that allows it to provide a pressure value that effectively combines inlet gas pressures 428, 430. Further, instructions 450 when executed cause microprocessor 410 to implement a patient effort algorithm using the I/O received via I/O interface 420, and providing a patient effort output 440. Such a patient effort algorithm may be, but is not limited to, the patient effort algorithms discussed above in relation to FIG. 2 and FIG. 4. As part of implementing the patient effort algorithm, instructions 450 cause microprocessor 410 to calculate a variety of otherwise unknown system parameters including, but not limited to, tubing compliance 412 ($C_T$), lung compliance 414 ($C_L$), lumped resistance 416 ($R_P$), and leakage 418 ($\lambda_{LEAK}$). The aforementioned system parameters may be used in a variety of interim calculations with the results of one or more of the interim calculations providing results that are predictive of patient effort output 440.

In addition, microprocessor based system 400 may include a graphical user interface driver 490 and a graphical user interface 495. Graphical user interface 495 may be any interface that provides for graphically portraying information from microprocessor based system 400 to a user. Thus, graphical user interface 495 may be any display known in the art. In some cases, graphical user interface 495 may further include an ability to receive input from a user. The ability to receive input may be provided by, for example, a touch screen capability, a keyboard, a mouse, and/or the like deployed in association with graphical user interface 495. Graphical user interface driver 490 may be any circuit, system or device known in the art that is capable of converting information from microprocessor based system 400 into graphical information displayable via graphical user interface 495.

Figure 6:
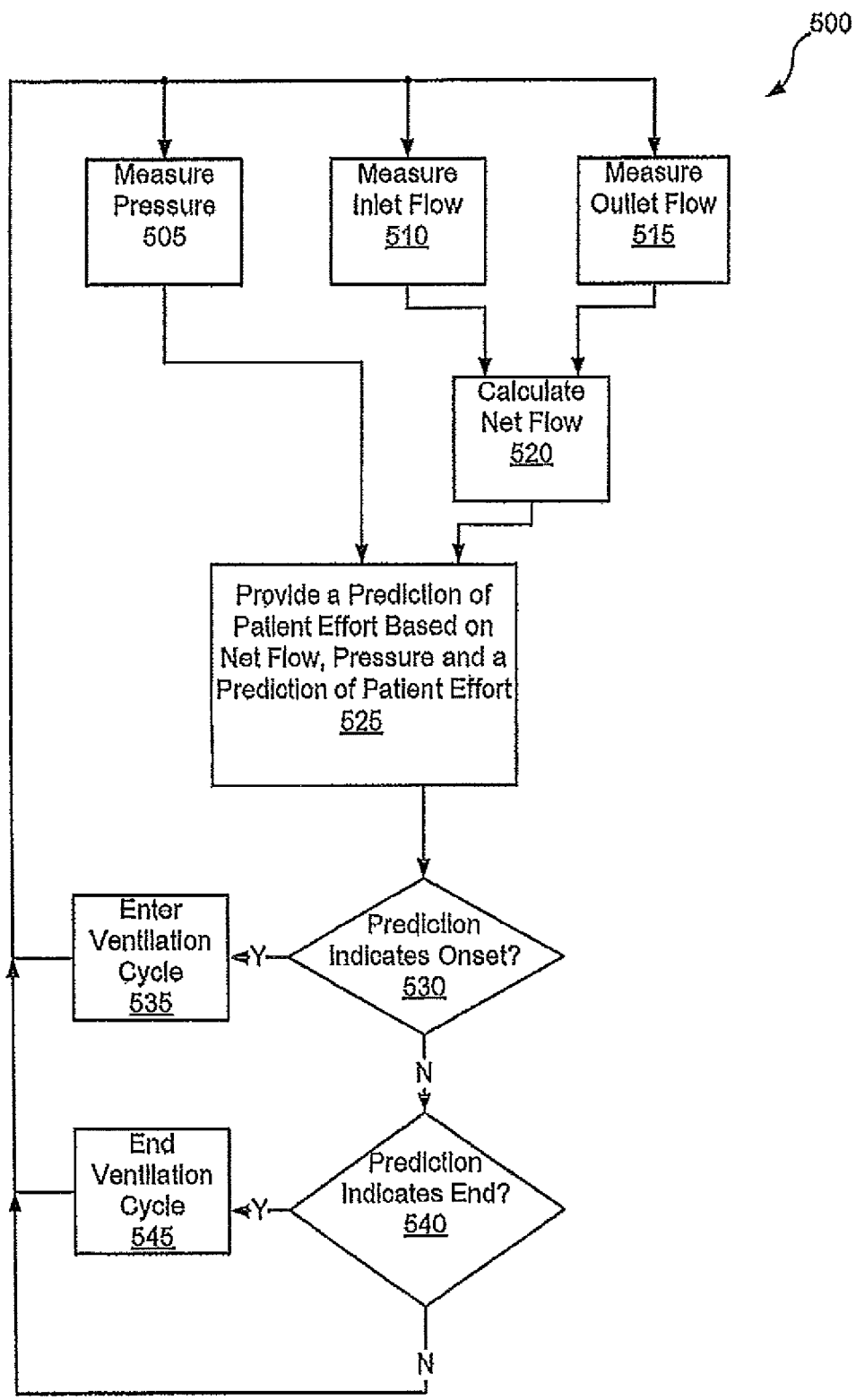
FIG. 6 is a flow diagram depicting a method in accordance with some embodiments of the present invention for triggering a ventilation cycle.

FIG. 6 is a flow diagram 500 depicting a method in accordance with some embodiments of the present invention for triggering a ventilation cycle. Following flow diagram 500, a pressure is measured (block 505), an inlet flow is measured (block 510), and an outlet flow is measured (block 515). In some cases, the pressure is measured in a tube connecting a ventilator to a person being ventilated In some cases, the pressure is measured near a gas inlet and/or near a gas outlet. In other cases, the pressure is measured near a junction of the gas inlet with the gas outlet. In various cases, the pressure measurement is a single point pressure measurement, while in other cases the pressure measurement is a multiple point pressure measurement and the measured pressure is a mathematical combination of two or more pressure measurements. Measuring the inlet flow may include measuring the flow of a single gas, or measuring the flows of two or more gases and aggregating the multiple flow values. Measuring the outlet flow may include, but is not limited to, measuring the flow of gas at the outlet of the ventilation system. The outlet flow is subtracted from the inlet flow at a particular instance to generate an instantaneous net flow (block 520).

The net flow and measured pressure for a given instant are used to calculate an updated prediction of patient effort (block 525). This process may be done using the approach discussed above in relation to FIG. 4. It is then determined whether the updated prediction of patient effort indicates an onset condition (block 530). Where an onset condition is indicated (block 530), a ventilation cycle is triggered to begin (block 535). As an example, the updated prediction of patient effort may be the filtered patient effort signal ($\phi_d$) that was discussed above. The filtered patient effort signal is a function of the derivative of patient effort ($\dot{p}_p$) as set forth in the following equation:

$$\varphi_d = b_{Pp}(s)\frac{\dot{p}_p(s)}{\Lambda(s)}.$$

Thus, the filtered patient effort signal is expected to be negative when the actual patient effort ($p_p$) is decreasing. Therefore, the onset of inspiration is indicated when the filtered patient effort signal becomes less than zero (e.g., exhibits a negative zero crossing where the signal transitions from a positive value to a negative value). This indicator may be used to synchronize the onset of a ventilation cycle with patient effort. Such synchrony results in improved patient ventilation. In some cases, a ventilation cycle is triggered to begin once the filtered patient effort signal is less than zero. In other cases, a ventilation cycle is triggered to begin once the filtered patient effort signal reaches a predefined negative threshold value or positive threshold value. It should be noted that while the filtered patient effort signal is used in the preceding example, that one or more other signals may be similarly used. For example, prediction error signal, $z-\hat{z}$ may also be used as it is similarly correlated with actual patient effort. Based on the disclosure provided herein, one of ordinary skill in the art will recognize a variety of other signals that may be used to initiate a ventilation cycle.

Alternatively, it is determined whether the updated prediction of patient effort indicates an end condition (block 540). Where an end condition is indicated (block 540), a previously started ventilation cycle is triggered to terminate (block 545). As an example, the updated prediction of patient effort may be the same filtered patient effort signal used to trigger the onset of inspiration. As the filtered patient effort signal is a function of the derivative of patient effort, the end of inspiration is indicated when the filtered patient effort signal becomes greater than zero (e.g., exhibits a positive zero crossing where the signal transitions from a negative value to a positive value). Such an indicator may be used to synchronize the termination of a ventilation cycle with patient effort, and thereby provide improved patient ventilation. In some cases, a ventilation cycle is triggered to end once the filtered patient effort signal is greater than zero. In other cases, a ventilation cycle is triggered to end once the filtered patient effort signal reaches a predefined negative threshold value or positive threshold value. Again, it should be noted that while the filtered patient effort signal is used in the preceding example, that one or more other signals may be similarly used. For example, prediction error signal, $z-\hat{z}$ may also be used as it is similarly correlated with actual patient effort. Based on the disclosure provided herein, one of ordinary skill in the art will recognize a variety of other signals that may be used to terminate a ventilation cycle.

Figure 7:
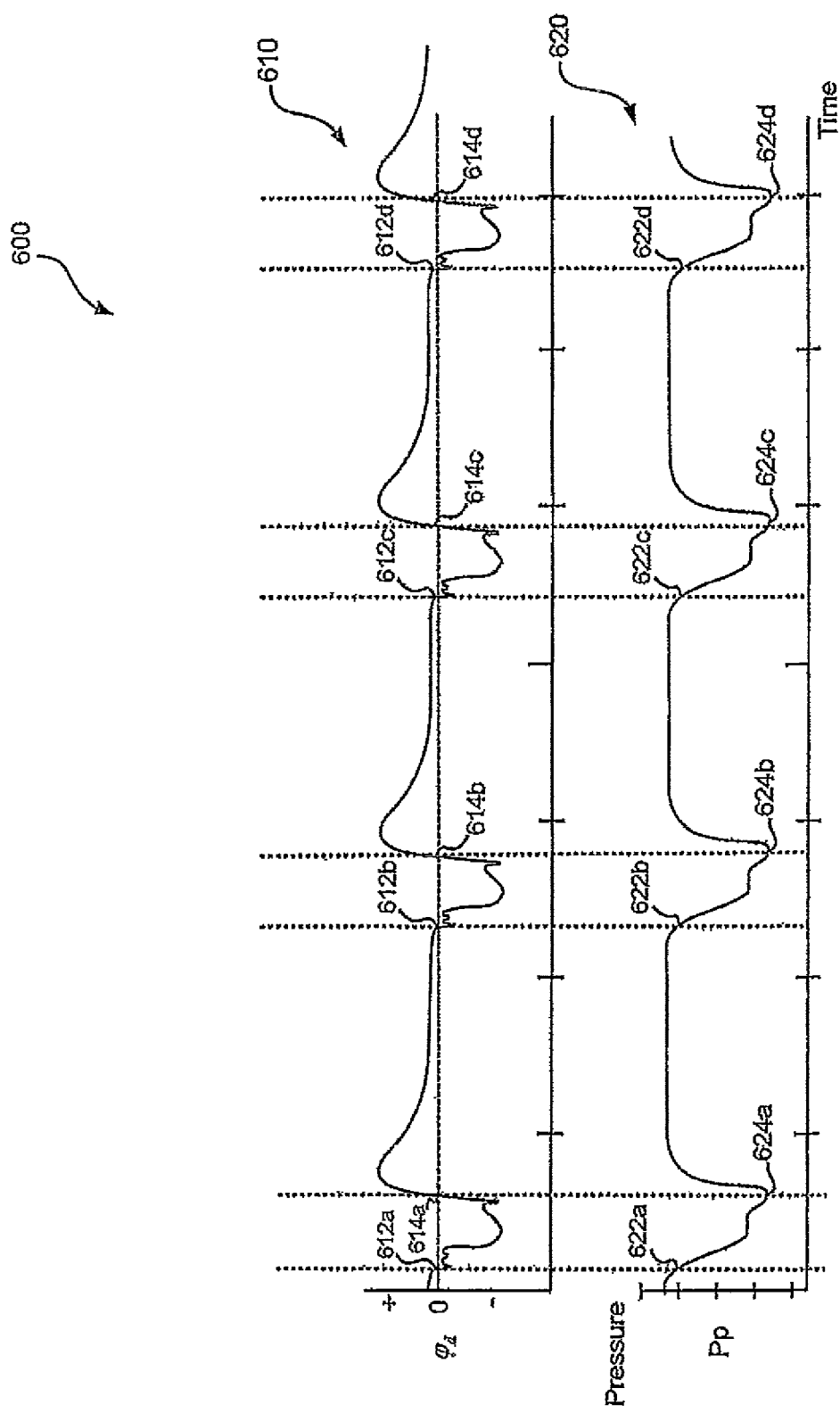
FIG. 7 is a timing diagram showing triggering a ventilation cycle based upon an estimated patient effort signal in accordance with various embodiments of the present invention.

Turning to FIG. 7, a timing diagram 600 shows the process of triggering multiple ventilation cycles based on a proxy of patient effort. In this case, the proxy of patient effort is the filtered patient effort signal ($\phi_d$) 610. A actual patient effort signal ($P_p$) 620 is shown to demonstrate the synchrony achievable using different embodiments of the present invention. It should be noted that while filtered patient effort signal 610 is shown as the ventilation trigger, that one or more other signals may be similarly used. For example, prediction error signal, $z-\hat{z}$, may also be used as it is similarly correlated with actual patient effort. Based on the disclosure provided herein, one of ordinary skill in the art will recognize a variety of other signals that may be used to effectuate triggering.

As shown, the transition of filtered patient effort signal 610 through a negative zero crossing point 612a corresponds to the beginning of an actual patient inspiration effort 622a. A subsequent positive zero crossing point 614a corresponds to the onset of exhalation 624a. This process is depicting for a number of ventilation cycles. Consistent with timing diagram 600, a positive zero crossing of filtered patient effort signal 610 may be used to trigger the beginning of a ventilation cycle, and a negative zero crossing of filtered patient effort signal 610 may be used to trigger the end of a ventilation cycle.

Figure 8:
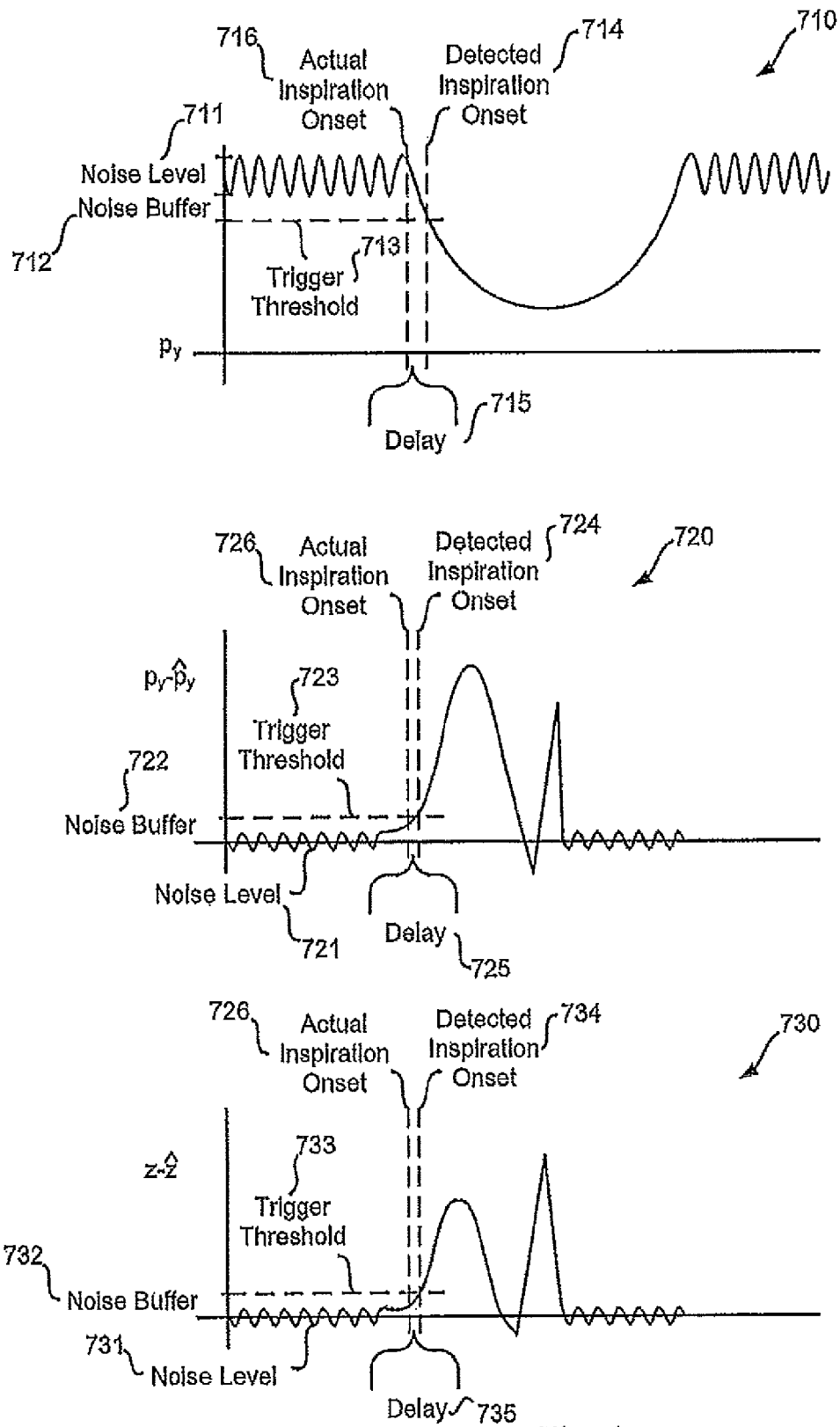
FIG. 8 are timing diagrams comparing a process triggering off of a pressure sensor verses triggering off of an estimated patient effort signal in accordance with one or more embodiments of the present invention.

FIG. 8 includes a timing diagram 710 showing a process of triggering off of a pressure sensor corresponding to $p_y$, a timing diagram 720 showing a process of triggering off of an estimated patient effort signal, $p_y-\hat{p}_y$, and a timing diagram 730 showing a process of triggering off of another signal correlated to patient effort, $z-\hat{z}$. As shown by timing diagram 710, the pressure sensor exhibits a noise level 711 with a trigger threshold 713 set a noise buffer amount 712 below the expected noise level 711 to avoid false triggering. As shown, the pressure corresponding to $p_y$ eventually drops below trigger threshold 713 resulting in a detected inspiration onset 714 (represented a vertical dashed line). Detected inspiration threshold 714 occurs a delay period 715 after an actual inspiration onset 716 (represented by a vertical dashed line). As can be seen from timing diagram 710, the magnitude of delay period 715 is a function of noise level 711 and noise buffer amount 712.

Noise associated with a pressure measurement is not necessarily correlated with that associated with flow measurements. By combining information derived from both pressure and flow measurements in the development of an estimated patient effort signal, the amount of noise expected is typically reduced when compared with the noise expected when only a single measurement is used. A noise buffer amount is often chosen based on the magnitude of expected noise. Thus, in some embodiments of the present invention, both the expected noise level and noise buffer amount are less than that exhibited in single measurement systems. The reduction of these variables allows for a detected inspiration that is correlated more closely in time with an actual inspiration onset. Timing diagrams 720, 730 graphically depict such a reduced trigger delay.

Following timing diagram 720, the estimated patient effort signal, $p_y-\hat{p}_y$, exhibits a relatively small noise level 721 with a trigger threshold 723 set a noise buffer amount 722 above the expected noise level 721 to avoid false triggering. As shown, the estimated patient effort signal eventually exceeds trigger threshold 723 resulting in a detected inspiration onset 724 (represented a vertical dashed line). Detected inspiration onset 724 occurs a delay period 725 after an actual inspiration onset 726 (represented by a vertical dashed line). Delay period 725 is less than that which results when only a single point of measurement is used. Similarly, following timing diagram 730, the estimated patient effort signal, $z-\hat{z}$, exhibits a relatively small noise level 731 with a trigger threshold 733 set a noise buffer amount 732 above the expected noise level 731 to avoid false triggering. As shown, the estimated patient effort signal eventually exceeds trigger threshold 733 resulting in a detected inspiration onset 734 (represented a vertical dashed line). Detected inspiration onset 734 occurs a delay period 735 after an actual inspiration onset 736 (represented by a vertical dashed line). Delay period 735 is less than that which results when only a single point of measurement is used.

Figure 9:
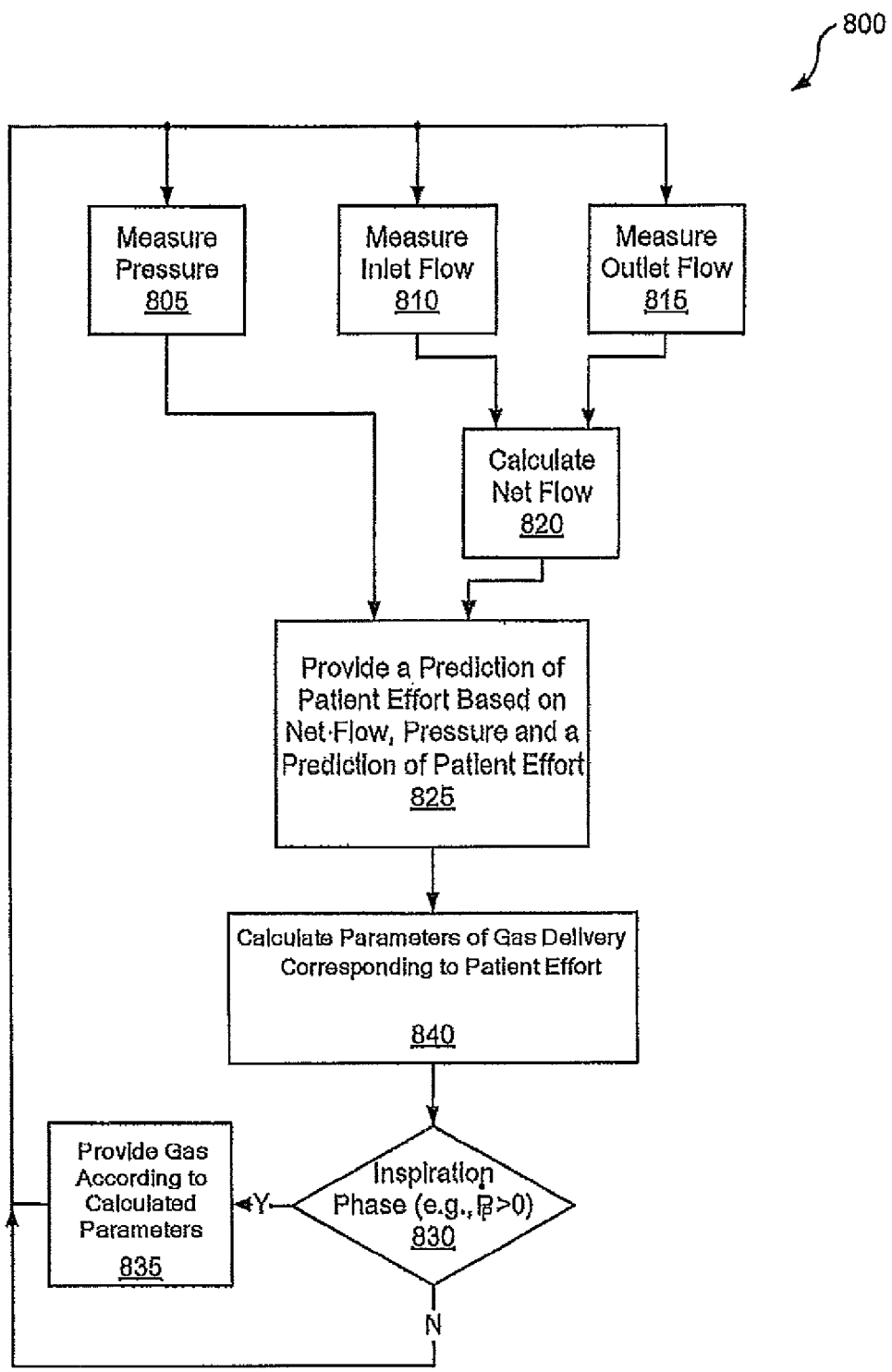
FIG. 9 is a flow diagram showing a method for providing ventilation in proportion to patient effort in accordance with various embodiments of the present invention.

Turning to FIG. 9, a flow diagram 800 shows a method for providing ventilation in proportion to patient effort in accordance with various embodiments of the present invention. Following flow diagram 800, a pressure is measured (block 805), an inlet flow is measured (block 810), and an outlet flow is measured (block 815). In some cases, the pressure is measured in a tube connecting a ventilator to a person being ventilated. In some cases, the pressure is measured near a gas inlet and/or near a gas outlet. In other cases, the pressure is measured near a junction of the gas inlet with the gas outlet. In various cases, the pressure measurement is a single point pressure measurement, while in other cases the pressure measurement is a multiple point pressure measurement and the measured pressure is a mathematical combination of two or more pressure measurements. Measuring the inlet flow may include measuring the flow of a single gas, or measuring the flows of two or more gases and aggregating the multiple flow values. Measuring the outlet flow may include, but is not limited to, measuring the flow of gas at the outlet of the ventilation system. The outlet flow is subtracted from the inlet flow at a particular instance to generate an instantaneous net flow (block 820).

The net flow and measured pressure for a given instant are used to calculate an updated prediction of patient effort (block 825). This process may be done using the approach discussed above in relation to FIG. 4. Desired gas delivery parameter(s) of gas to be delivered by the ventilator an instant corresponding to the calculated patient effort is/are then calculated (block 840). In some embodiments of the present invention, the gas delivery parameters are flow and/or pressure. In this case, a desired pressure and flow of gas delivery are each a function of patient effort. For example, where patient effort is determined to be a value at an instant x described by a function $f(x)$, then the calculated pressure may be described at an instant using the function $g(f(x))$ and the calculated flow at an instant may be described by the function $h(f(x))$. In one particular embodiment of the present invention, the function g and the function h are each constant multipliers. In such a case, the calculated pressure at an instant x is $k_1 f(x)$ and the calculated flow at the instant x is $k_2 f(x)$, where $k_1$ is the constant corresponding to pressure and $k_2$ is the constant corresponding to flow. Based on the disclosure provided herein, one of ordinary skill in the art will recognize other functions g functions h that may be used in relation to different embodiments of the present invention. The pressure used as a metric for delivering gas may be, but is not limited to, wye pressure or patient lung pressure. The flow used as a metric for delivering gas may be, but is not limited to, patient lung flow or inlet gas flow.

It is then determined whether the updated prediction of patient effort indicates an inspiration phase (block 830). In some embodiments of the present invention, an inspiration phase is indicated where the derivative of patient effort $\dot{p}_P$ is greater than zero. Where an inspiration phase is indicated (block 830), gas is delivered to a recipient in accordance with the gas delivery parameters previously calculated (block 835). Again, gas delivery parameters may include, but are not limited to, pressures and flows of gas or gas components (e.g., oxygen, air, nitrogen, helium, etc.) to be delivered to a patient. Otherwise, where an inspiration phase is not indicated (block 830), gas delivery is not provided. Such an approach provides for gas delivery at a rate and/or pressure as a function of the patient's effort. Such an approach provides for increased patient comfort as well as less interference with a patient's own attempts at breathing.

Figure 10:
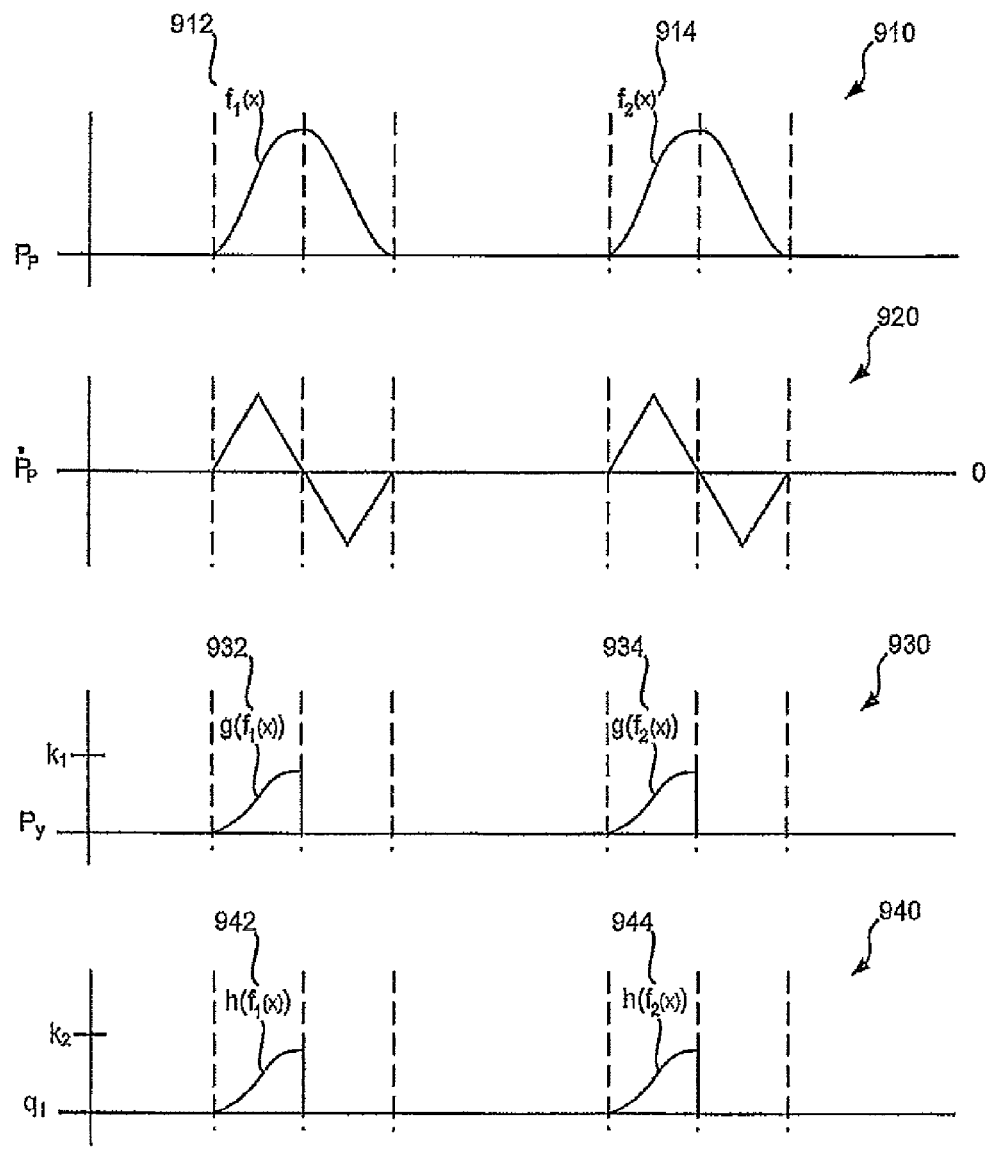
FIG. 10 illustrates a group of timing diagrams that graphically depict providing ventilation in proportion to patient effort in accordance with one or more embodiments of the present invention.

Turning to FIG. 10, four timing diagrams 910, 920, 930, 940 graphically depict providing ventilation in proportion to patient effort in accordance with one or more embodiments of the present invention. Timing diagram 910 depicts patient effort as a function of time, and timing diagram 920 depicts a derivative of patient effort as a function of time. As shown, when the derivative of patient effort is greater than zero (corresponding to an inspiration phase), patient effort is described as a function $f(x)$. It should be noted that while timing diagram 910 shows patient effort as the same function repeating over time, that a first instance of $f_1(x)$ 912 may differ substantially from the second instance of $f_2(x)$ 914 depending upon the breathing pattern of the particular patient.

A timing diagram 930 depicts an effort by a ventilator to increase the pressure at the wye connection to offset a pressure decrease caused by patient effort. As shown, during the inspiration phase (i.e., when the derivative of patient effort is greater than zero), the ventilator attempts to raise the pressure at the wye connection as a function of patient effort, $g(f_1(x))$ 932. On a subsequent breath, the ventilator attempts to raise the pressure at the wye as a function of patient effort, $g(f_2(x))$ 934. In this particular case, the function g is a constant $k_1$, however, other time varying functions may be used in accordance with different embodiments of the present invention.

Similarly, during the inspiration phase, the ventilator increases the flow of gas to a patient as a function of patient effort, $h(f_1(x))$ 942. On a subsequent breath, the ventilator increases the flow of gas to a patient as a function of patient effort, $h(f_2(x))$ 944. In this particular case, the function h is a constant $k_2$, however, other time varying functions may be used in accordance with different embodiments of the present invention. In some cases, the functions g and h may be proportional or inversely proportional to patient effort. It should be noted that in the sense that gas delivery is provided as a function of patient effort, that patient effort may be determined based directly on patient effort (i.e., patient interpleural pressure), or on a first or higher order derivative of patient effort.

Figure 11:
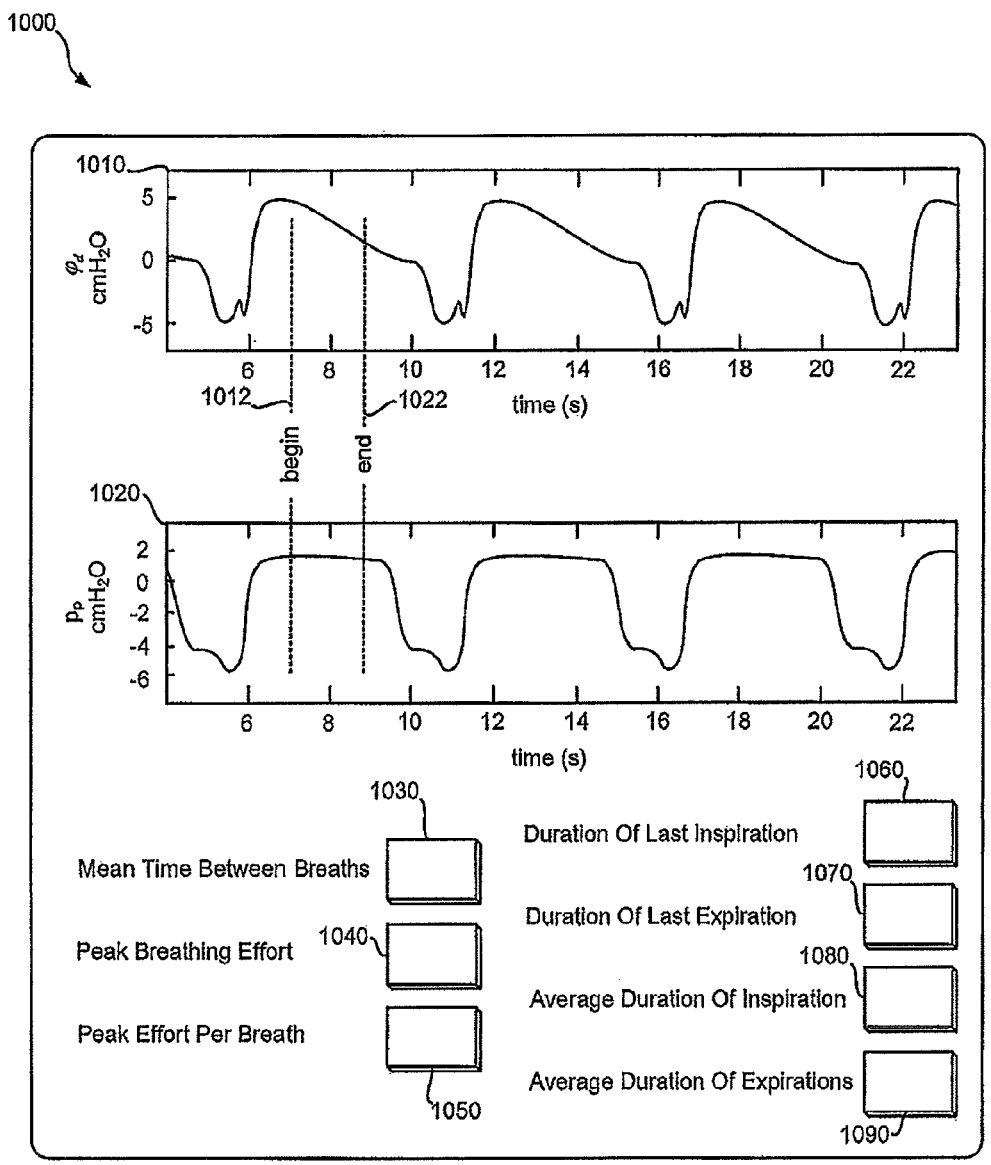
FIG. 11 shows an exemplary graphical interface showing the display of patient effort corresponding to an actively breathing patient in accordance with some embodiments of the present invention.

Turning to FIG. 11, an exemplary graphical interface 1000 showing the display of patient effort corresponding to an actively breathing patient in accordance with some embodiments of the present invention. Graphical interface 1000 includes a graphical display of filtered patient effort ($\phi_d$) 1010, and patient effort ($p_p$) 1020 each as a function of time. It should be noted that other indications of patient effort may be displayed in addition to those depicted or in place of those depicted depending upon the particular embodiment of the present invention.

In the depicted embodiment, time is displayed across a horizontal axis and the value of the respective patient effort value is displayed across a left axis. As time proceeds, the time increments across the horizontal axis are updated to reflect a window around the current time. In addition, two user movable vertical bars 1012, 1022 are disposed over graph 1010 and graph 1020. This allows a user to place a begin bar 1012 and an end bar 1022 at particular times to measure an event. The time difference between begin bar 1012 and end bar 1022 may be displayed to the user, along with the value of filtered patient effort and patient effort at the respective instants in time. In some cases, begin bar 1012 and end bar 1022 may be used via a keyboard command or a mouse command. Based on the disclosure provided herein one of ordinary skill in the art will recognize a variety of I/O that may be used to manipulate begin bar 1012 and end bar 1022 in relation to graphs 1010, 1020.

In addition, various metrics relating to the graphically displayed patient effort may be calculated and displayed via graphical interface 1000. For example, a mean time between breaths 1030 may be calculated and displayed. Such a mean time may be calculated based on a defined number of breaths, where a time between each of the breaths is calculated from the end of expiration to the beginning of subsequent inspiration. Based on the disclosure provided herein, one of ordinary skill in the art will appreciate a variety of approaches that may be used to calculate mean time between breaths in accordance with different embodiments of the present invention. As another example, a peak breathing effort 1040 may be displayed. Peak breathing effort 1040 may be the maximum value recorded on either of graph 1010 or graph 1020 over the course of a defined number of breaths depending upon the particular implementation. As yet another example, peak effort per breath 1050 may be displayed. Peak effort per breath 1050 may indicate the peak value of either graph 1010 or graph 1020 for a most current breath. Alternatively it may indicate the peak value of either graph 1010 or graph 1020 for a breath identified by begin bar 1012. As yet a further example, a duration of last inspiration 1060 may be displayed. Duration of the last inspiration 106 indicates a time from when the onset of inspiration was detected until the end of inspiration was detected for the most recent breath. In one case, this may be achieved by detecting when a first derivative of the patient effort exceeds a threshold until it returns below the threshold. As another example, a duration of the last expiration 1070 may be displayed. In some cases, duration of the last expiration 1070 may be calculated by detecting when a first derivative of the patient effort falls below a threshold until the time when the first derivative returns above the threshold. As another example, an average duration of inspiration 1080 and an average duration of expiration 1090 may be displayed. The may be calculated by averaging a number of the previously discussed expiration durations and inspiration durations.

Figure 12:
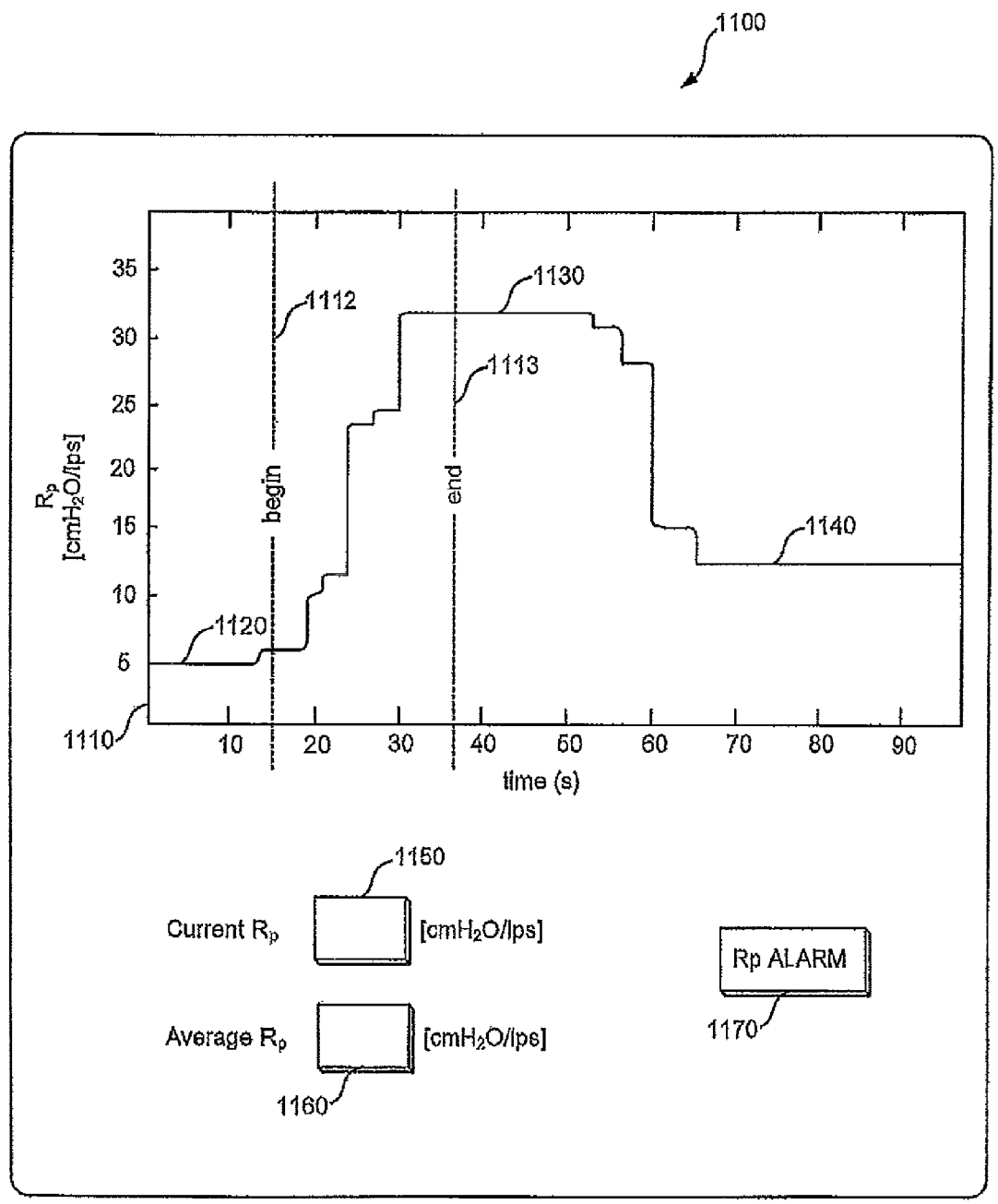
FIG. 12 shows an exemplary graphical interface showing the display of a respiratory parameter corresponding to an actively breathing patient in accordance with some embodiments of the present invention.

Turning to FIG. 12, an exemplary graphical interface 1100 showing the display of a respiratory parameter corresponding to an actively breathing patient in accordance with some embodiments of the present invention. In particular, a graph 1110 depicts an estimated value of the patient resistance parameter as a function of time. In some embodiments, the patient resistance parameter is referred to as "estimated Rp" because it is the result of calculation as distinguished from the actual value of the patient resistance. It should be noted that while graphical interface 1100 is described as showing estimated Rp, that other respiratory parameters may be displayed in accordance with different embodiments of the present invention. For example, graphical interface 1100 may be augmented to display lung compliance or leakage parameters, with these additionally displayed parameters determined using the same or similar set of equations as described herein. Based on the disclosure provided herein, one of ordinary skill in the art will recognize a variety of respiratory parameters that may be displayed. In some cases, the displayed respiratory parameters may be used by a monitoring clinician for real time assessment of a patient. Alternatively, or in addition, the displayed respiratory parameters may be used to determine a potential system malfunction or to indicate a disconnect of the patient from the ventilator. As one particular example, a dramatic increase in Rp may indicate a partial obstruction. Based on the disclosure provided herein, one of ordinary skill in the art will recognize a variety of advantages that may be achieved in accordance with one or more embodiments of the present invention.

As shown, time is displayed across a horizontal axis and the value of estimated Rp is displayed across a left axis. In some embodiments, as time proceeds, the time increments across the horizontal axis are updated to reflect a window around the current time. Additionally, in some embodiments, two user movable vertical bats 1112, 1113 are disposed over graph 1110. This allows a user to place a begin bar 1112 and an end bar 1113 at particular times to measure an event. The time difference between begin bar 1112 and end bar 1113 may be displayed to the user, along with the value of filtered patient effort and patient effort at the respective instants in time. In some cases, begin bar 1112 and end bar 1113 may be used via a keyboard command or a mouse command. Based on the disclosure provided herein one of ordinary skill in the art will recognize a variety of I/O that may be used to manipulate begin bar 1112 and end bar 1113 in relation to graph 1110.

In this particular example, for an initial period 1120 estimated Rp is initialized with a value of five (5) cmH$_2$O/lps. At this time, the actual value of Rp is nearer to thirty (30) cmH$_2$O/lps. Over a period of time, the algorithm used to determine the value of estimated Rp adaptively adjusts until the estimated value approximates the actual value for Rp during a period 1130. Sometime around the fifty (50) second mark, an obstruction is removed from the ventilation system resulting in a dramatic decrease in the actual value of Rp. At this point, the algorithm adaptively adjusts by lowering the value of estimated Rp until the estimated value approximates the actual value. During a period 1140, the value of estimated Rp remains approximately constant near the actual value of Rp.

In addition, various metrics relating to the graphically displayed resistance parameter may be calculated and displayed via graphical interface 1100. For example, a current Rp value 1150 may be displayed, and an average Rp value 1160 may be displayed. Average Rp value 1160 may be calculated by averaging a number of values for Rp over a particular time period. In addition, a visual alarm 1170 may be displayed. Such a visual alarm may be triggered whenever a predefined increase or decrease in the value of estimated Rp is detected. It should be noted that graphical interface 1100 may be augmented to display a variety of other information.

The present invention provides novel systems, methods and devices delivering a gas in proportion to a patient effort. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:
1. A ventilation system, comprising:
   a processor communicably coupled to a computer readable medium, wherein the computer readable medium includes instructions executable by the processor to:
   receive a measured pressure value;
   receive a net flow value;
   calculate a patient effort value based on a relationship between patient effort, the measured pressure value, the net flow value, and an estimated normalized prediction error, wherein the estimated normalized prediction error is based at least in part on a current estimated value of a parameter vector; and
   calculate a gas delivery metric, wherein the gas delivery metric varies as a function of the patient effort value; and
   cause a gas to be delivered consistent with the gas delivery metric.

2. The system of claim 1, wherein the gas delivery metric is selected from: pressure, and flow.

3. The system of claim 2, wherein the flow is selected from: patient lung flow and inlet gas flow.

4. The system of claim 2, wherein the pressure is selected from: lung pressure and wye pressure.

5. The ventilation system of claim 1, wherein the computer readable medium further includes instructions executable by the processor to: determine an inhalation phase based on the patient effort value.

6. The ventilation system of claim 5, wherein the inhalation phase is indicated when the calculated patient effort value is greater than zero.

7. The ventilation system of claim 5, wherein the system is operable to deliver the gas during the determined inhalation phase.

8. The ventilation system of claim 1, wherein a function of the patient effort value is a constant multiplier.

9. The ventilation system of claim 1, wherein a function of the patient effort value is a non-linear function.

10. The ventilation system of claim 1, wherein a function of the patient effort value is a time varying function.

11. The ventilation system of claim 1, wherein the patient effort value is further calculated based on a combination of one or more intermediate values calculated using the measured pressure value and the net flow value, the one or more intermediate values selected from: a filtered pressure value and a regression vector.

12. The ventilation system of claim 1, wherein the relationship is a parameterized system input to output relationship.

13. The method of claim 12, wherein the parameterized system input to output relationship is the regression form: $z = \Theta^T \Phi + \Phi_d$, wherein z is a filtered pressure value, $\Theta$ is a current estimated value of a parameter vector, $\Phi$ is at least a part of regression vector, and $\Phi_d$ is a filtered patient effort.

14. The method of claim 13, wherein the parameterized system input to output relationship is derived from a transfer function.

15. The ventilation system of claim 14, wherein the transfer function is derived from a model:

$$\begin{bmatrix} \dot{p}_Y \\ \dot{p}_L \end{bmatrix} = \begin{bmatrix} -\frac{1}{C_T R_P} & \frac{1}{C_T R_P} \\ \frac{1}{C_L R_P} & -\frac{1}{C_L R_P} \end{bmatrix} \begin{bmatrix} p_Y \\ p_L \end{bmatrix} +$$

$$\begin{bmatrix} \frac{1}{C_T} & \frac{1}{C_T} & -\frac{1}{C_T} \\ 0 & 0 & 0 \end{bmatrix} \begin{bmatrix} q_{AIR} \\ q_{O2} \\ q_E \end{bmatrix} + \begin{bmatrix} 0 & -\frac{1}{C_T} & 0 \\ 1 & 0 & -\frac{1}{C_T} \end{bmatrix} \begin{bmatrix} \dot{p}_P \\ q_{Tleak} \\ q_{Pleak} \end{bmatrix}$$

wherein $p_y$ is a value for a wye gas pressure, $p_L$ is a value of a pressure in a patient's lungs, $\dot{p}_y$ is a value for a first derivative of a wye gas pressure, $\dot{p}_L$ is a value for a first derivative of pressure in the patient's lungs, $C_T$ is a value for a tubing compliance, $C_L$ is a value for a lung compliance, $R_P$ is a value for a patient resistance, $q_{air}$ is a value for an inlet flow of air, $q_{o2}$ is a value for an inlet flow of oxygen, $q_E$ is a value for an outlet gas flow, $q_{Tleak}$ is a value for gas flow associated with tubing leakage, $q_{Pleak}$ is a value for gas flow associated with leakage in the patient, and $\dot{p}_P$ is a value for the derivative of patient effort.

16. A method for respiratory support, the method comprising:
measuring a pressure and providing a measured pressure;
measuring an inlet flow and an outlet flow, and providing a measured net flow;
using a relationship between a first value related to the measured pressure, a second value related to the measured net flow and an estimated normalized prediction error, wherein the estimated normalized prediction error is based at least in part on a current estimated value of a parameter vector to calculate an estimate of patient effort from the measured pressure and measured net flow; and supplying a gas in proportion to the estimate of patient effort.

17. The method of claim 16, wherein supplying the gas in proportion to the estimate of patient effort includes supplying the gas at a pressure in proportion to the estimate of patient effort.

18. The method of claim 16, wherein supplying the gas in proportion to the estimate of patient effort includes supplying the gas at a flow in proportion to the estimate of patient effort.

19. The method of claim 16, wherein the estimate of patient effort is further based on a combination of one or more intermediate values derived from the measured pressure and measured net flow, the one or more intermediate values selected from: a filtered pressure value and a regression vector.

20. The method of claim 16, wherein the second value is selected from: a filtered version of the measured net flow, and the measured net flow.

21. The method of claim 16, wherein the first value is selected from: a filtered version of the measured pressure, and the measured pressure.

22. The method of claim 16, wherein the relationship is a parameterized system input to output relationship.

23. The method of claim 22, wherein the parameterized system input to output relationship is the regression form: $z=\Theta^T \Phi + \Phi_d$, wherein z is a filtered pressure value, $\Theta$ is a current estimated value of a parameter vector, $\Phi$ is at least a part of regression vector, and $\Phi_d$ is a filtered patient effort.

24. The method of claim 23, wherein the parameterized system input to output relationship is derived from a transfer function.

25. The method of claim 24, wherein the transfer function is derived from the model:

$$\begin{bmatrix} \dot{p}_Y \\ \dot{p}_L \end{bmatrix} = \begin{bmatrix} -\frac{1}{C_T R_P} & \frac{1}{C_T R_P} \\ \frac{1}{C_L R_P} & -\frac{1}{C_L R_P} \end{bmatrix} \begin{bmatrix} p_Y \\ p_L \end{bmatrix} +$$

$$\begin{bmatrix} \frac{1}{C_T} & \frac{1}{C_T} & -\frac{1}{C_T} \\ 0 & 0 & 0 \end{bmatrix} \begin{bmatrix} q_{AIR} \\ q_{O2} \\ q_E \end{bmatrix} + \begin{bmatrix} 0 & -\frac{1}{C_T} & 0 \\ 1 & 0 & -\frac{1}{C_T} \end{bmatrix} \begin{bmatrix} \dot{p}_P \\ q_{Tleak} \\ q_{Pleak} \end{bmatrix}$$

wherein $p_y$ is a value for a wye gas pressure, $p_L$ is a value of a pressure in a patient's lungs, $\dot{p}_y$ is a value for a first derivative of a wye gas pressure, $\dot{p}_L$ is a value for a first derivative of pressure in the patient's lungs, $C_T$ is a value for a tubing compliance, $C_L$ is a value for a lung compliance, $R_p$ is a value for a patient resistance, $q_{air}$ is a value for an inlet flow of air, $q_{o2}$ is a value for an inlet flow of oxygen, $q_E$ is a value for an outlet gas flow, $q_{Tleak}$ is a value for gas flow associated with tubing leakage, $q_{Pleak}$ is a value for gas flow associated with leakage in the patient, and $\dot{p}_p$ is a value for the derivative of patient effort.

26. A ventilation system, the system comprising:
a gas inlet;
a gas outlet;
a tube coupling the gas inlet and the gas outlet;
a pressure sensor, wherein the pressure sensor is operable to provide a measured pressure value indicating a pressure in the tube;
a first flow sensor, wherein the first flow sensor is operable to provide an inlet flow value indicating a flow associated with the gas inlet;
a second flow sensor, wherein the second flow sensor is operable to provide an outlet flow value indicating a flow associated with the gas outlet; and
a processor communicably coupled to a computer readable medium, wherein the computer readable medium includes instructions executable by the processor to:
receive a measured pressure value;
receive a net flow value;
calculate a patient effort value based on a relationship between patient effort, the measured pressure value, the net flow value, and an estimated normalized prediction error, wherein the estimated normalized prediction error is based at least in part on a current estimated value of a parameter vector;
calculate a gas delivery metric that varies as a first function of the patient effort value;
determine an inhalation phase based on the patient effort value; and
cause a gas to be delivered consistent with the gas delivery metric.

27. A method for respiratory support, the method comprising:
measuring a pressure associated with a patient circuit connected to a patient and providing a measured pressure;
measuring an inlet flow and an outlet flow associated with the patient circuit, and providing a measured net flow;
calculating a patient effort value based on the measured pressure and the measured net flow using a relationship between a first value related to the measured pressure, a second value related to the measured net flow and patient effort, and an estimated normalized prediction error, wherein the estimated normalized prediction error is based at least in part on a current estimated value of a parameter vector; and
delivering a volume of respiratory gas over a period of time to the patient through the patient circuit based on the patient effort.

28. The method of claim 27, wherein delivering a volume further comprises:
delivering a volume of respiratory gas proportional to the patient effort.

29. The method of claim 27, wherein delivering a volume further comprises:
identifying a target volume of gas proportional to the patient effort.

30. The method of claim 29, further comprising:
adjusting flow of gas in the patient circuit based on the target volume.

31. The method of claim 27, wherein delivering a volume further comprises:
delivering a flow of respiratory gas to the patient through the patient circuit based on the patient effort.

32. The method of claim 27, wherein delivering a volume further comprises:
delivering a flow of respiratory gas to the patient through the patient circuit proportional to the patient effort.

33. A ventilation system, the ventilation system comprising:
a processor communicably coupled to a computer readable medium, wherein the computer readable medium includes instructions executable by the processor to:
receive a measured pressure value;
receive a net flow value;
calculate a patient effort value based on a relationship between patient effort, the measured pressure value, the net flow value, and an estimated normalized prediction error, wherein the estimated normalized prediction error is based at least in part on a current estimated value of a parameter vector;
calculate a volume of gas to be delivered based on the patient effort; and
cause a gas to be delivered consistent with the calculated volume of gas.

34. The system of claim 33 wherein the calculated volume of gas is proportional to the patient effort.

35. The system of claim 33 wherein the processor causes a gas to be delivered by adjusting a pressure in a patient circuit of the ventilation system.

36. The system of claim 33 wherein the processor causes a gas to be delivered by adjusting a flow of gas in a patient circuit of the ventilation system.

* * * * *